(12) United States Patent
Boursnell et al.

(10) Patent No.: US 6,344,445 B1
(45) Date of Patent: *Feb. 5, 2002

(54) HERPES VIRUS VECTORS AND THEIR USES

(75) Inventors: Michael Edward Griffith Boursnell, Cambridge (GB); Malcolm Keith Brenner, Memphis, TN (US); Dagmar Dilloo, Düsseldorf (DE); Stephen Charles Inglis, Cambridge (GB)

(73) Assignees: Cantab Pharmaceutical Research Limited, Cambridge (GB); St. Jude Children's Research Hospital, Memphis, TN (US)

(*) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 08/734,054

(22) Filed: Oct. 18, 1996

Related U.S. Application Data

(60) Provisional application No. 60/005,649, filed on Oct. 19, 1995.

(51) Int. Cl.$^7$ .......................... A61K 31/70; C12N 15/86
(52) U.S. Cl. ........................................ 514/44; 435/456
(58) Field of Search ........................... 514/44; 435/456, 435/472

(56) References Cited

U.S. PATENT DOCUMENTS 5,672,344 A * 9/1997 Kelley et al. .............. 424/93.2

FOREIGN PATENT DOCUMENTS

| EP | 0 176 170 | 4/1986 |
| EP | 0 259 212 | 3/1988 |
| EP | 0 420 911 | 4/1991 |
| WO | 86/07610 | 12/1986 |
| WO | 88/00971 | 2/1988 |
| WO | 89/12109 | 12/1989 |
| WO | 90/09441 | 8/1990 |
| WO | 91/02796 | 3/1991 |
| WO | 92/05273 | 4/1992 |
| WO | 92/10564 | 6/1992 |
| WO | 94/12649 | 6/1994 |
| WO | 94/16716 | 8/1994 |
| WO | WO 96/26267 | 10/1996 |

OTHER PUBLICATIONS

Glorioso et al, Viral Vectors, Academic Press, San Diego, California, pp. 1–23, 1995.*
Orkin et al, Report and Recommendations of the Panel to assess the NIH Investment in Research on gene Therapy, released by NIH, 41 unnumbered pages, Dec. 7, 1995.*
Verma et al, Nature, vol. 389, pp. 239–242, Sep. 18, 1997.*
Anderson, Nature, vol. 392, Supplement, pp. 25–30, Apr. 30, 1998.*
Mire–Sluis, "Cytokines and Disease," *Trends in Biotechnology*, 11(3):74–77 (1993).
van Der Bruggen et al., "A Gene Encoding an Antigen Recognized by Cytolytic T Lymphocytes on a Human Melanoma," *Science*, 254:1643–1647 (1991).
Randazzo et al., "Treatment of Experimental Intracranial Murine Melanoma with a Neuroattenuated Herpes Simplex Virus 1 Mutant," *Virology*, 211:94–101 (1995).
Livingston, "Construction of Cancer Vaccines with Carbohydrate and Protein (Peptide) Tumor Antigens," *Current Opinion in Immunology*, 4:624–629 (1992).
Moore, "The Clinical Use of Colony Stimulating Factors," *Annu. Rev. Immunol.*, 9:159–191 (1991).
Alt et al., "A Pair of Selectable Herpesvirus Vectors for Simultaneous Gene Expression in Human Lymphoid Cells," *Gene*, 102:265–269 (1991).
Burchell et al., "A Short Sequence, Within the Amino Acid Tandem Repeat of a Cancer–Associated Mucin, Contains Immunodominat Epitopes," *Int. J. Cancer*, 44:691–696 (1989).
van der Bruggen et al., "Molecular Definition of Tumor Antigens Recognized by T Lymphocytes," *Current Opinion in Immunology*, 4:608–612 (1992).
Boon, "Toward a Genetic Analysis of Tumor Rejection Antigens," *Advances in Cancer Research*, 58:177–210 (1992).

* cited by examiner

*Primary Examiner*—Terry McKelvey
(74) *Attorney, Agent, or Firm*—Klarquist Sparkman, LLP

(57) ABSTRACT

A process of treating a human or non-human animal cell to introduce heterologous genetic material into said cell and express said material in said cell, comprises (a) providing a recombinant herpesviral vector which is an attenuated or replication-defective and non-transforming mutant herpesvirus, and which carries heterologous genetic material, and (b) transducing human or non-human animal cells selected from: hemopoietic cells, malignant cells related to blood cells, and malignant or non-malignant CD34+cells; by contacting said cells with said virus vector to transduce said cells and express said genetic material. Among applications of the technique is modification of hemopoietic cells by transfer of genes, e.g. to generate tumor immunogens from malignant cells.

16 Claims, 8 Drawing Sheets

CD34+ Marrow cells

Day +7

MOI 0.1

HERPES VIRUS VECTORS AND THEIR USES

This application claims priority under 35 USC § 119(e) from provisional application No. 60/005,649, filed Oct. 19, 1995, herein incorporated by reference.

FIELD OF THE INVENTION

This invention relates to viral vectors and methods for their use, especially for example for transducing cells, for example malignant cells of hemopoietic lineage, and for inducing the expression of foreign genetic material in such cells. The invention also relates to pharmaceutical compositions based on such viral vectors, to the production of cells infected with such viral vectors, to pharmaceutical preparations based on such cells, and to their use for administration to humans and to non-human animals in order to achieve expression of foreign genetic material in vivo. Methods according to the invention can be used for example in cancer immunotherapy.

BACKGROUND OF THE INVENTION

Recombinant viral vectors are among several known agents available for the introduction of foreign genes into cells so that they can be expressed as protein. A central element is the target gene itself under the control of a suitable promoter sequence that can function in the cell to be transduced. Known techniques include non-viral methods, such as simple addition of the target gene construct as free DNA; incubation with complexes of target DNA and specific proteins designed for uptake of the DNA into the target cell; and incubation with target DNA encapsulated for example in liposomes or other lipid-based transfection agents.

A further option is the use of recombinant virus vectors engineered to contain the required target gene, and able to infect the target cells and hence carry into the cell the target gene in a form that can be expressed. A number of different viruses has been used for this purpose including retroviruses, adenoviruses, and adeno-associated viruses.

Specification EP 0 176 170 (Institut Merieux: B Roizman) describes foreign genes inserted into a herpes simplex viral genome under the control of promoter-regulatory regions of the genome, thus providing a vector for the expression of the foreign gene. DNA constructs, plasmid vectors containing the constructs useful for expression of the foreign gene, recombinant viruses produced with the vector, and associated methods are disclosed.

Specification EP 0 448 650 (General Hospital Corporation: Al Geller, XO Breakefield) describes herpes simplex virus type 1 expression vectors capable of infecting and being propagated in a non-mitotic cell, and for use in treatment of neurological diseases, and to produce animal and in vitro models of such diseases.

Recombinant viruses are known in particular for use in (e.g. corrective) gene therapy applied to gene deficiency conditions.

Examples of genes used or proposed to be used in corrective gene therapy include: the gene for human adenosine deaminase (ADA), as mentioned in for example WO 92/10564 (KW Culver et al: US Secretary for Commerce & Cellco Inc), and WO 89/12109 & EP 0 420 911 (IH Pastan et al); the cystic fibrosis gene and variants described in WO 91/02796 (L-C Tsui et al: HSC Research & University of Michigan), in WO 92/05273 (F S Collins & J M Wilson: University of Michigan) and in WO 94/12649 (RJ Gregory et al: Genzyme Corp).

The prior art of malignant tumor treatment includes studies that have highlighted the potential for therapeutic vaccination against tumors using autologous material derived from a patient's own tumor. The general theory behind this approach is that tumor cells may express one or more proteins or other biological macromolecules that are distinct from normal healthy cells, and which might therefore be used to target an immune response to recognise and destroy the tumor cells.

These tumor targets may be present ubiquitously in tumors of a certain type. A good example of this in cervical cancer, where the great majority of tumors express the human papillomavirus E6 and E7 proteins. In this case the tumor target is not a self protein, and hence its potential as a unique tumor-specific marker for cancer immunotherapy is clear.

There is increasing evidence that certain self proteins can also be used as tumor target antigens. This is based on the observation that they are expressed consistently in tumor cells, but not in normal healthy cells. Examples of these include the MAGE family of proteins. It is expected that more self proteins useful as tumor targets remain to be identified.

Tumor associated antigens and their role in the immunobiology of certain cancers are discussed for example by P van der Bruggen et al, in Current Opinion in Immunology, 4(5) (1992) 608–612. Other such antigens, of the MAGE series, are identified in T. Boon, Adv Cancer Res 58 (1992) pp 177–210, and MZ2-E and other related tumor antigens are identified in P. van der Bruggen et al, Science 254 (1991) 1643–1647; tumor-associated mucins are mentioned in PO Livingston, in current Opinion in Immunology 4 (5) (1992) pp 624–629; e.g. MUC1 as mentioned in J Burchell et al, Int J Cancer 44 (1989) pp 691–696.

Although some potentially useful tumor-specific markers have thus been identified and characterised, the search for new and perhaps more specific markers is laborious and time-consuming.

An experimental intracranial murine melanoma has been described as treated with a neuroattenuated HSV1 mutant 1716 (BP Randazzo et al, Virology 211 (1995) pp 94–101), where the replication of the mutant appeared to be restricted to tumor cells and not to occur on surrounding brain tissue.

Administration to mammals of cytokines as such (i.e. as protein) has been tried, but is often poorly tolerated by the host and is frequently associated with a number of side-effects including nausea, bone pain and fever. (A Mire-Sluis, TIBTech vol. 11 (1993); MS Moore, in Ann Rev Immunol 9 (1991) 159–91). These problems are exacerbated by the dose levels often required to maintain effective plasma concentrations.

It is known to modify live virus vectors to contain genes encoding a cytokine or a tumor antigen. Virus vectors have been proposed for use in cancer immunotherapy to provide a means for enhancing tumor immunoresponsiveness. Specification WO 86/07610 (Transgene: MP Kieny et al) discloses expression of human IL-2 in mammalian cells by means of a recombinant poxvirus comprising all or part of a DNA sequence coding for a human IL-2 protein. Specification EP 0 259 212 (Transgene SA: R Lathe et al) discloses viral vectors of the pox, adeno or herpes types, for controlling tumors, containing a heterologous DNA sequence coding for at least the essential regions of a tumor-specific protein. Specification WO 88/00971 (CSIRO, Australian National University: Ramshaw et al) discloses recombinant vaccine comprising a pox, herpes or adeno virus vaccine vector, especially vaccinia, including a nucleotide sequence expressing at least part of an antigenic polypeptide and a second sequence expressing at least part of a lymphokine (interleukin 1, 2, 3 or 4, or gamma interferon) which increases immune response to the antigenic polypeptide; and specification WO 94/16716 (E Paoletti et al: Virogenetics Corp.) describes attenuated recombinant vaccinia viruses containing DNA coding for a cytokine or a tumor antigen, e.g. for use in cancer therapy.

It has been proposed to use GMCSF-transduced tumor cells as a therapeutic vaccine against renal cancer. The protocols for corresponding trials involve removal of tumor material from the patients, and then transduction with the appropriate immunomodulator gene. The engineered cells are then to be re-introduced into the patient to stimulate a beneficial immune response.

Vectors based on herpesvirus saimiri, a virus of non-human primates, have been described as leading to gene expression in human lymphoid cells (B Fleckenstein & R Grassmann, Gene 102(2) (1991), pp 265–9). However, it has been considered undesirable to use such vectors in a clinical setting.

Although it is therefore known to introduce immunomodulatory and other genes into cells such as certain kinds of tumor cells, existing methods of achieving this are considered by the present inventors to have limitations, whether the difficulties are due to low quantitative amounts of transduction, to complexity, or to undesirable side-effects of the systems employed.

The present inventors consider that it has been difficult up to now to introduce genes into a number of kinds of cells, e.g. tumor cells of hemopoietic lineage, such as leukaemias, or to do this efficiently, e.g. for purposes of corrective gene therapy or cancer immunotherapy.

For the transfer of genes to such cells as hemopoietic progenitor cells, retroviral vectors have been the most widely tried vectors up to the present. It appears that these vectors however do not integrate and are not expressed in nondividing cells, and this limits their value e.g. when used with for example hemopoietic stem cells (HSCs) or primary cells from human hemopoietic malignancies as targets for gene transfer and expression. In order to overcome this limitation, culture of target cells, e.g. HSCs, with hemopoietic growth factors such as cytokines has been tried, with a view to induce the HSCs into cycle and increase the efficiency of retrovirus-mediated gene transfer to these target cells, but unfortunately the cytokines in the culture media appear to have induced differentiation with loss of the desired self-renewal capacity of the cells.

Thus, adeno-associated viral vectors have been proposed for use instead of retroviral vectors, but it has appeared that the efficiency of integration of such vectors is low.

Also, the present inventors consider, on the basis of recent experience with adenoviral vectors, that these have limitations. Thus, while they can infect approximately 50% of hemopoietic cells under certain conditions, nevertheless gene expression is often delayed for several days. It has also been found in certain tests that transduction of a heterologous gene into acute leukaemia cells by a recombinant adenovirus vector or a retrovirus vector led to either negligible or at best about 3% transduction yield, and that thus there can be a problem of efficiency of transduction yield with such vectors.

The Present Invention

The present inventors consider that the prior art leaves it still desirable to provide further viral vectors and processes for their use in transforming human and animal cells. In particular, it remains desirable to provide materials and methods to produce gene transfer to human and non-human animal cells with useful rapidity. Also desirable is to provide materials and methods to produce gene transfer with useful efficiency. Also desirable is the provision of materials and methods to produce gene transfer with applicability to a useful range of target cell types, usefully including for example non-dividing cells.

According to an aspect of the invention described herein, target cells for transduction by herpesviral vectors can be chosen for example from among cells of hemopoietic lineages; from lymphoid or myeloid cells, from stem cells or CD34+ cells, e.g. cell preparations containing such cells, as for example obtained or prepared in connection with bone-marrow transplantation; or cells of neuroectodermal origin, especially malignant such cells, and transduced with viral vectors as described herein. In this use, it has been found that certain methods and procedures according to examples of the invention can lead to surprisingly high transduction efficiency.

In one aspect the present invention aims to provide materials and methods to facilitate the use of tumor cells as immunogens and vaccines. In a further aspect the invention aims to facilitate the transduction of cells of hemopoietic lineage and provide useful compositions and procedures based thereon.

The present invention also aims to provide means for creating immunogens and therapeutic vaccines that can be used to induce immune responses against tumor-specific antigens, e.g. in patients with pre-existing tumors.

The invention is particularly applicable for example for gene transfer into hemopoietic cells such as lymphoid cells, that are nonpermissive for expression of late lytic genes of herpesvirus such as herpes simplex virus.

According to an aspect of the invention there is provided a process of treating a human or non-human animal cell to introduce heterologous genetic material, e.g. material comprising a heterologous gene, into said cell, e.g. to express said genetic material in said cell, comprising the steps of (a) providing a recombinant herpesviral vector which is an attenuated or replication-defective and non-transforming mutant herpesvirus, and which carries heterologous genetic material, e.g. a gene encoding a heterologous protein, and (b) transducing human or non-human animal cells selected from: hemopoietic cells, malignant cells related to blood cells, and malignant or non-malignant CD34+ cells; by contacting said cells with said virus vector to transduce said cells. In embodiments of the invention described below said genetic material is then expressed in said cell. Transduction takes place by infection of the live target cell by the viral vector in per-se known manner.

Such a process can for example comprise treating a human or non-human animal cell to introduce heterologous genetic material into said cell to render said cell more highly immunogenic, comprising the steps of (a) providing a recombinant herpesviral vector which is an attenuated or replication-defective and non-transforming mutant herpesvirus, and which carries e.g. a gene encoding a heterologous immunomodulatory protein selected from cytokines and immunological co-stimulatory molecules and chemo-attractants, and (b) transducing malignant or non-malignant human or non-human animal cells, which can be selected for example from: malignant cells related to blood cells, hemopoietic cells, malignant or non-malignant CD34+ cells, by contacting said cells with said virus vector to transduce said cells and render said cells more highly immunogenic.

Pharmaceutical preparations provided and used according to certain embodiments of the invention, for use in transducing human or non-human animal cells selected from: hemopoietic cells; malignant cells related to blood cells; and malignant or non-malignant CD34+ cells; can comprise a recombinant herpesviral vector which is an attenuated or replication-defective and non-transforming mutant herpesvirus, and which carries heterologous genetic material, e.g. a gene encoding a heterologous protein.

Pharmaceutical preparations provided and used according to certain embodiments of the invention can comprise human or non-human animal cells selected from: hemopoietic cells; malignant cells related to blood cells; and malignant or non-malignant CD34+ cells; said cells having been infected with a recombinant herpesviral vector which is an attenuated or replication-defective and non-transforming mutant herpesvirus, and which carries e.g. a gene encoding a heterologous protein.

Also within the invention is a process of treating a subject which is a human subject or a non-human animal subject in order to achieve expression of a foreign gene in vivo, comprising administering to said subject a pharmaceutical composition of the kinds mentioned above and described herein; and a process of treating a subject which is a human subject or a non-human animal subject in order to elicit an immune response, which comprises administering to said subject a pharmaceutical composition of the kinds mentioned above and described herein.

An aspect of the invention concerns provision and use of a recombinant herpesvirus vector, e.g. based on a non-transforming herpesvirus, carrying a gene encoding a protein, e.g. an immunomodulatory protein, or a protein useful for expression in connection with gene therapy: also provided by the invention is its use in transducing cells to render them more highly immunogenic; among the cells that can usefully be treated in this way are for example malignant cells of human and non-human animals, especially for example malignant cells related to blood cells, e.g. leukaemic cells, or hemopoietic cells, including CD34+ cells, whether malignant or non-malignant. Thus suitable cells for treatment include for example hemopoietic progenitor cells such as healthy CD34+ cells, which when transduced with herpesvirus vectors carrying a heterologous gene that it is desired to express in the treated cell, can carry a high copy number of the heterologous gene, enabling homologous recombination with the genome of the treated cell without the need for an integrase.

Among the applications of embodiments of the present invention is the modification of malignant hemopoietic cells by the transfer of genes to generate tumor immunogens. Among the substances that can usefully be generated in a modified cell to function as a tumor immunogen are GM-CSF and interleukin 2. For example, it has been reported that interleukin 2 production by tumor cells bypasses T helper function in the generation of an antitumor response (ER Fearon et al, Cell 60 (1990) pp 397 et seq), and it has been reported in the case of murine GM-CSF (G Dranoff et al, Proc Nat Acad Sci USA 90 (1993) pp 3539 et seq.) that vaccination with irradiated tumor cells engineered to secrete GM-CSF stimulates potent, specific and long lasting anti-tumor immunity.

Thus, according to embodiments of the invention, a recombinant herpesvirus, for example a recombinant HSV, can be used as a vector for transduction of (for example) leukaemia cells so as to produce expression of inserted genetic material, e.g. a gene encoding an immunomodulatory protein or other protein relevant to cancer immunotherapy or gene therapy, in such cells.

In particular examples of the invention, a recombinant herpes simplex virus, whether HSV1 or HSV2, engineered to contain a heterologous gene as part of its genome, can be used to deliver the gene with good efficiency to leukaemia cells, to evoke effective expression of the heterologous gene within the tumor cells, and the transduced cells can then be used for example as a cellular immunogen such as a vaccine for cancer immunotherapy, and thereby, among other effects, mediate immune effects on tumor cells other than cells infected with the virus vector. Thus the invention also provides useful methods for gene transduction of leukaemia cells among others.

Also provided according to certain embodiments of the invention are methods of using a recombinant herpesvirus such as HSV, e.g. a replication-defective herpesvirus such as replication-defective HSV, whether HSV1 or HSV2, for transduction of various cell types based on cells of hemopoietic lineage, and other cell types, e.g. neuroblastomas, e.g. to introduce immunomodulatory genes, or other genes for the purpose of gene therapy or cancer immunotherapy, into such cells.

It has also been found that transduction into leukemia cells using an example of a HSV-based recombinant vector can be achieved successfully using fresh tumor cells. Thus, tumor cells, which can be cells that (prior to transduction) either have not been incubated at all under cell culture conditions, or else have not been incubated for more than a few hours (e.g. not more than about 2 or up to 4 hours, or not incubated as long as overnight), e.g. freshly-sampled tumor cells, can be exposed to a recombinant herpesvirus vector as mentioned herein carrying suitable genetic material. This can be genetic material that is not being expressed, or is not being substantially expressed, by the tumor cells, e.g. genetic material encoding an immunomodulatory protein such as for example GM-CSF, thereby to infect the cells with the recombinant herpesvirus vector; and the resulting infected cells can be used for example either for reinfusion into the subject from whom the parent cells were obtained, or for reaction with leukocytes in vitro.

For example, freshly sampled human leukaemia cells can be exposed to a virus vector carrying a gene encoding human GM-CSF or inter alia one of the other immunomodulatory proteins mentioned herein, and reinfused into the patient as an immunogenic cell preparation, e.g. using some or all of the procedural steps mentioned below, with a useful extent of transduction of the cells. By contrast, previously, using a corresponding retrovirus vector, it has proved necessary to culture the tumor cells in vitro for some days before they could be transduced usefully; e.g. in order to drive cells into cell division and render them susceptible to retroviral transduction.

This can be a useful advantage of recombinant herpesvirus vectors as described herein, since it can reduce the need for laboratory manipulation of the tumor cells, can be more rapid, with more efficient cell transduction, and can present a more viable clinical treatment option.

Cytotoxic T-cells can be activated and/or expanded, e.g. in vitro, e.g. for purposes of cancer immunotherapy, by the use of virally-transduced presenting or target cells, e.g. especially target cells of hemopoietic lineage, CD34+ cells, where the virus used for transduction is a vector as described herein carrying a gene encoding an antigen relevant to the desired therapy, e.g. an antigen encoded by EBV or HPV, and in addition, if desired, encoding an immunomodulatory protein as mentioned herein. An example of such use is the case of donor-cell tumors in transplant patients where the tumor cells express EBV or HPV antigens: donor T-lymphocytes can be activated and expanded in relation to target cells, e.g. of types as mentioned above, expressing EBV or HPV antigens as a result of transduction by viral vectors as described herein carrying corresponding heterologous genes, e.g. HPV E6 or E7 genes. Recombinant herpesvirus as mentioned herein can also transduce other tumor cell types, such as neuroblastoma cells, with good efficiency.

The recombinant herpesvirus used as a vector according to this invention can contain a gene encoding an immunomodulatory protein, or other protein relevant to cancer immunotherapy or gene therapy.

Genes encoding any of several immunomodulatory proteins can be used in this way to render tumor cells immunogenic, in humans and non-human animals. The resulting immune responses can be used in prevention and treatment of tumor growth.

Immunomodulators are molecules that can enhance or repress immunological responses. They include cytokines (soluble glycoproteins which initiate or enhance activation, growth and differentiation of immune system cells), co-stimulatory molecules (structures present on the surface of cells within the body that interact with immune cells to help stimulate immune responses) and (immunological) chemo-attractant molecules which serve to attract immune cells to sites of immune or inflammatory activity, e.g. at which antigens can be presented. "Immunomodulating" or "immunomodulatory" protein, as referred to herein, includes one or more proteins which can enhance a host's immune response, e.g. to a mutant virus, or to an antigen such as an immunogen from a pathogen or source exogenous to the virus, or to a tumor associated antigen, which can for example be produced by the mutant virus. The immunomodulating proteins are not those presently used as immunogens in themselves. The immunodulating proteins for which encoding nucleotide sequences are expressibly carried by viruses as described herein can for example usefully have sequences native to the species which is to receive vaccination by the recombinant viruses, or which is otherwise to receive cells transduced with the recombinant viruses, e.g. it is recommended to use an immunomodulating protein of substantially human sequence for transducing a cell preparation to be used as a human immunogen or vaccine, or to be used otherwise in connection with humans.

Any hazards associated with expression of such proteins in a fully replicating virus are eliminated where the virus is a replication defective mutant. In certain embodiments, the proteins can be selected to enhance the effect of the mutant virus as an immunogen or vaccine in the context in which it is employed.

Examples of useful immunomodulating proteins include cytokines for example interleukins 1 to 15 (IL1 to IL15), interferons alpha, beta or gamma, tumor necrosis factor (TNF), granulocyte-macrophage colony stimulating factor (GM-CSF), macrophage colony stimulating factor (M-CSF), granulocyte colony stimulating factor (G-CSF), chemokines such as neutrophil activating protein (NAP), macrophage chemoattractant and activating factor (MCAF), RANTES, macrophage inflammatory peptides MIP-1 a and MIP-1 b, complement components and their receptors, accessory molecules such as one of the B7 family of T cell co-stimulators such as B7.1 or B7.2, ICAM-1, 2 or 3, OX40 ligand and cytokine receptors. Where nucleotide sequences encoding more than one immunomodulating protein are inserted, they may comprise more than one cytokine or may be a combination of cytokine(s) and accessory molecule(s). Many further kinds of immunomodulatory proteins and genes can be useful in this invention.

Examples of particularly useful immunomodulatory proteins include GMCSF; IL2; IL4; IL7; IL12; B7.1; TNF-alpha; interferon gamma; CD40L; and lymphotactin.

The genetic material encoding an immunomodulatory protein can be carried in the mutant viral genome as an expressible open reading frame encoding a hybrid or fusion protein which comprises a polypeptide region having homology to and functionality of an immunomodulatory protein, linked to a polypeptide region having another homology and optionally another functionality. For example, the immunomodulatory protein can be, comprise, or correspond in functionality to the gp34 protein identified as a binding partner to human OX-40 (see W Godfrey et al, J Exp Med 180(2) 1994 pp 757–762, and references cited therein, including S Miura et al, Mol Cell Biol 11(3) 1991, pp 1313–1325). The version of this protein functionality that can be encoded in the mutant viral genome can correspond to the natural gp34 sequence itself, or to a fragment thereof, or to a hybrid expression product e.g. based on the (C-terminal) extracellular (binding) domain of gp34 fused to another protein, e.g. to the constant region of an immunoglobulin heavy chain such as human IgG1, e.g. with the extracellular domain of gp34 (a type 2 membrane protein) fused at its N-terminal to the C-terminal of the immunoglobulin constant domain.

Others of the immunomodulatory proteins can also be carried and expressed in corresponding or other derivative and hybrid forms. It is also understood that mutations of the aminoacid sequences of such immunomodulatory proteins can be incorporated. Included here are proteins having mutated sequences such that they remain homologous, e.g. in sequence, function, and antigenic character, with a protein having the corresponding parent sequence. Such mutations can preferably for example be mutations involving conservative aminoacid changes, e.g. changes between aminoacids of broadly similar molecular properties. For example, interchanges within the aliphatic group alanine, valine, leucine and isoleucine can be considered as conservative. Sometimes substitution of glycine for one of these can also be considered conservative. Interchanges within the aliphatic group aspartate and glutamate can also be considered as conservative. Interchanges within the amide group asparagine and glutamine can also be considered as conservative. Interchanges within the hydroxy group serine and threonine can also be considered as conservative. Interchanges within the aromatic group phenylalanine, tyrosine and tryptophan can also be considered as conservative. Interchanges within the basic group lysine, arginine and histidine can also be considered conservative. Interchanges within the sulphur-containing group methionine and cysteine can also be considered conservative. Sometimes substitution within the group methionine and leucine can also be considered conservative. Preferred conservative substitution groups are aspartate-glutamate; asparagine-glutamine; valine-leucine-isoleucine; alanine-valine; phenylalanine-tyrosine; and lysine-arginine. In other respects, mutated sequences can comprise insertion and/or deletions.

Particular useful examples of derivative and hybrid forms include proteins with sequences having deleted therefrom any of: a transmembrane segment, an intracellular sequence portion, an N-terminal or C-terminal sequence, e.g. a sequence of from 1–5 aminoacids upwards; and/or sequences having added thereto any of e.g. an N-terminal or C-terminal sequence, e.g. a sequence of from 1–5 aminoacids upwards, or a further functional sequence e.g. as described above.

Suitably the immunomodulating protein can comprise a cytokine, e.g. granulocyte macrophage colony stimulating factor (GM-CSF). Murine GM-CSF gene, for example, encodes a polypeptide of 141 amino acids, the mature secreted glycoprotein having a molecular weight of between 14k-30k daltons depending on the degree of glycosylation. GM-CSF is a member of the hemopoietic growth factor family and was first defined and identified by its ability to stimulate in vitro colony formation in hemopoietic progenitors. GM-CSF is a potent activator of neutrophils, eosinophils and macrophage-monocyte function, enhancing migration, phagocytosis, major histocompatibility complex (MHC) expression, and initiating a cascade of bioactive molecules which further stimulate the immune system. Human GM-CSF is currently being evaluated in the clinic for the treatment of neutropenia following chemotherapy and as an adjuvant in cancer therapy. The heterologous nucleotide sequence employed may comprise a heterologous gene, gene fragment or combination of genes.

The invention is also applicable to corrective gene therapy, to improve the target cell's usefulness or viability. For example, normal CD34+ cells can be transduced with viral vector as described herein encoding a DNA repair enzyme such as 06-methylguanine DNA methyltransferase (MGMT), for protection of target cells e.g. during chemotherapy e.g. with nitrosourea, see T Moritz et al, Cancer Res 55(12) (1995) pp 2608–2614; R Maze et al, Proc Nat Acad Sci USA 93(1) 1996 206–210; or against radiation damage. Other genes for corrective gene therapy, of the kinds mentioned above, may also be transduced as transferred to target cells.

Heterologous DNA, e.g. further DNA, can usefully be introduced into the virus vector for other purposes, e.g. to encode expressibly an integrase such as one that is known to be able to act to integrate viral-vector DNA into the host genome so that the vector DNA becomes propagated when host cell mitosis occurs; and for other purposes.

Furthermore, according to embodiments of the invention, there are provided materials and methods to insert corrective or lethal genetic material to destroy or modulate malignant blast cells. This can be done for example by the expression in the target cell, by means of the herpesviral vector methods described herein, of antisense RNA or ribozyme sequences corresponding to genetic material encoded by the vector: for example as indicated in D Marcola et al, 'Antisense Approaches to Cancer Gene Therapy', Cancer Gene Ther 2 (1995) pp 47 et seq.

Techniques for use of antisense polynucleotides are known per se, and are readily adaptable to the specificity needed for the present application by using suitable nucleotide sequences, e.g. of at least about 12 nucleotides complementary in sequence to the sequence of a chosen target; by choosing from among known promoters suitable to the cellular environment in which they are to be effective, and other measures well known per se.

For example, techniques for use of antisense RNA to disrupt expression of a target gene are indicated (in connection with a sialidase gene) in specification WO 94/26908 (Genentech: TG Warner et al). Techniques for using antisense oligonucleotides capable of binding specifically to mRNA molecules are also indicated in specification. WO 94/29342 (La Jolla Cancer Research Foundation and the Regents of the University of Michigan: R Sawada et al) (in particular connection with mRNA encoding human lamp-derived polypeptides). Techniques for antisense oligonucleotides complementary to target RNA are indicated in specification WO 94/29444 (Department of Health and Human Services: B Ensoli and R Gallo) (as applied to basic fibroblast growth factor RNA). Techniques for using antisense oligonucleotides having a sequence substantially complementary to an mRNA which is in turn complementary to a target nucleic acid, in order to inhibit the function or expression of the target, are indicated in WO 94/24864 (General Hospital Corporation: HE Blum et al), (as applied to inhibition of hepatitis B viral replication). A review of antisense techniques is given by D Mercola and J S Cohen, ch.7 pp 77–89 in in R E Sobol and K J Scanlon (eds.) 'Internet Book of Gene Therapy: Cancer Therapeutics' (Appleton & Lange, Stamford, Connecticut, 1995). Applications to other target specificities are readily accessible by adaptation.

Techniques for using ribozymes to disrupt gene expression are also known per se. For example, techniques for making and administering ribozymes (or antisense oligonucleotides) in order to cleave a target mRNA or otherwise disrupt the expression of a target gene are indicated in specification WO 94/13793 (Apollon: C J Pachuk et al) (as applied to ribozymes that target certain mRNAs relevant to leukemias). A review of ribozyme techniques is given in M Kashani-Sabet and K J Scanlon, ch. 8 pp 91–101 in RE Sobol and K J Scanlon (eds.) 'Internet Book of Gene Therapy: Cancer Therapeutics' (Appleton & Lange, Stamford, Conn., 1995). Here also, applications to other target specificities are readily accessible by adaptation.

A lethal gene can also be inserted into the vector to destroy the transduced cell: for example a gene that is lethal in connection with an administered pharmaceutical, as described in e.g. specification WO 95/14100 (Wellcome Foundation: C Richards et al), exemplifying a gene encoding cytosine deaminase (CDA) under control of a CEA promoter, which when introduced into a cell is lethal in connection with administration of 5-fluorocytosine, transformed by the CDA into toxic 5-fluorouracil.

The recombinant herpesvirus used to carry a gene encoding an immunomodulatory protein or other genetic material as discussed herein, is preferably an attenuated and/or replication-defective herpesvirus.

The mutant herpesvirus can usefully be a mutant of any suitable herpesvirus; e.g. a non-transforming mutant of a mammalian herpesvirus; e.g. a mutant of a non-transforming human herpesvirus, especially for example a coated or enveloped mutant herpesvirus. Examples of herpesviruses of which mutants are provided and can be used as vectors according to embodiments of the invention include herpes simplex virus of type 1 (HSV-1) or type 2 (HSV-2), a human or animal cytomegalovirus (CMV), e.g. human cytomegalovirus (HCMV), varicella zoster virus (VZV), and/or human herpesvirus 6 and 7. EBV is less desirable, except in the form of a non-transforming mutant, because of its normally transforming properties. Animal viruses of which mutants are provided according to embodiments of the invention include pseudorabies virus (PRV), equine and bovine herpesvirus including EHV and BHV types such as IBRV, and Marek's disease virus (MDV) and related viruses.

The nomenclature of the genes of herpesviruses and their many corresponding homologues is diverse, and where the context admits, mention of a gene in connection with a herpesvirus includes reference, in connection with other herpesviruses possessing a homologue of that gene, to the corresponding homologue.

Suitable herpesviruses to be used as a basis for recombination to produce a vector suitable for use according to the present invention include defective herpesviruses conforming with the general or specific directions in specification WO 92/05263 (Inglis et al: Immunology Limited) (the disclosure of which is incorporated herein by reference), which describes for example the use as an immunogen or vaccine of a mutant virus whose genome is defective in respect of a gene essential for the production of infectious virus, such that the virus can infect normal host cells and undergo replication and expression of viral antigen genes in such cells but cannot produce infectious virus. WO 92/05263 particularly describes an HSV virus which is disabled by the deletion of a gene encoding the essential glycoprotein H (gH) which is required for virus infectivity (A Forrester et al, J Virol 66 (1992) 341–348). In the absence of gH protein expression non-infectious virus particles providing almost the complete repertoire of viral proteins are produced. These progeny particles, however, are not able to infect host cells and spread of the virus within the host is prevented. Such a virus has been shown to be an effective immunogen and vaccine in animal model systems (Farrell et al, J Virol 68 (1994) 927–932; McLean et al, J Infect Dis, 170 (1994) 1100–9).

Such mutant viruses can be cultured in a cell line which expresses the gene product in respect of which the mutant virus is defective.

The literature also describes cell lines expressing proteins of herpes simplex virus: the gB glycoprotein (Cai et al, in J Virol 61 (1987) 714–721), the gD glycoprotein (Ligas and Johnson, in J Virol 62 (1988) 1486) and the Immediate Early protein ICP4 (Deluca et al, in J Virol 56 (1985) 558). These too have been shown capable of supporting replication of viruses inactivated in respect of the corresponding genes.

Complete or substantial sequence data has been published for several viruses such as human cytomegalovirus CMV (Weston and Barrell in J Mol Biol 192 (1986) 177–208), varicella zoster virus VZV (AJ Davison and Scott, in J Gen Virol 67 (1986) 759–816) and herpes simplex virus HSV (McGeoch et al, in J. Gen. Virol. 69 (1988) 1531–1574 and further references cited below). The gH glycoprotein is known to have homologues in CMV and VZV (Desai et al, in J Gen Virol 69 (1988) 1147).

Suitable examples of such genes are genes for essential viral glycoproteins, e.g. (late) essential viral glycoproteins such as gH, gL, gD, and/or gB, and other essential genes. Essential and other genes of human herpesviruses are identifiable from DJ McGeoch, 'The Genomes of the Human Herpesviruses', in Ann Rev Microbiol 43 (1989) pp 235–265; DJ McGeoch et al, Nucl Acids Res 14 (1986) 1727–1745; D J McGeoch et al, J mol Biol 181 (1985) 1–13, for data and references cited therein. Reference is also made to data for homologues of gH glycoprotein in for example CMV and VZV, published e.g. in Desai et al, J Gen Virol 69 (1988) 1147).

Also useful as virus vectors in the present invention are for example the mutants such as HSV-1 mutant (in1814) unable to trans-induce immediate early gene expression, and essentially avirulent when injected into mice, described by C I Ace et al, J Virol 63(5) 1989 pp 2260–2269. Specification WO 91/02788 (CM Preston & CI Ace: University of Glasgow) describes useful HSV1 mutants including in 1814 capable of establishing latent infection in a neuronal host cell and of causing expression of an inserted therapeutic gene. Further examples of virus vectors useful in the invention are based on a mutation in a herpesvirus immediate early gene, e.g. a gene corresponding to ICP0, ICP4, ICP22 and ICP27. Mutations can be used in combination, e.g. as disclosed in WO 96/04395 (P Speck: Lynxvale), incorporated by reference. Also suitable as virus vectors for use in the present invention are such neuroattenuated HSV1 mutants as mutant 1716 (BP Randazzo et al, Virology 211 (1995) pp 94–101).

For herpesviruses reference is further made to data published for example in respect of human cytomegalovirus CMV (Weston and Barrell in J Mol Biol 192 (1986) 177–208), and varicella zoster virus VZV (AJ Davison et al, in J Gen Virol 67 (1986) 759–816).

According to certain examples of the present invention as described in further detail below, a genetically inactivated virus immunogen such as a vaccine provides an useful carrier for genes encoding immunomodulatory proteins. The virus vaccine can infect cells of the vaccinated host leading to intracellular synthesis of the immunomodulatory proteins. If the genetically inactivated vaccine is also acting as a vector for delivery of foreign antigens, then the immune response against the foreign antigen may be enhanced or altered.

Since these replication defective viruses can undergo only a single cycle of replication in cells of the vaccinated host, and fail to produce infectious new virus particles, production of the immunomodulatory proteins is confined to the site of vaccination, in contrast to the situation with a replication competent virus, where infection may spread. Furthermore, the overall amounts of immunomodulatory protein produced, though locally sufficient to stimulate a vigorous immune response, will be less than that produced by a replication competent virus, and less likely to produce adverse systemic responses.

In such a preferred embodiment, the heterologous nucleotide sequence, usually comprising a gene encoding immunomodulatory or other protein, is inserted into the genome of the mutant virus at the locus of the deleted essential gene, and most preferably, the heterologous nucleotide sequence completely replaces the gene which is deleted in its entirety. In this way, even if any unwanted recombination event takes place, and results in the reinsertion of the deleted gene from a wild source into the mutant virus, it would be most likely to eliminate the inserted heterologous nucleotide sequence. This would avoid the possibility that a replication competent viral carrier for the heterologous nucleotide sequence would be produced. Such a recombination event would be extremely rare, but in this embodiment, the harmful effects of such an occurrence would be minimised.

Materials and methods according to the invention can be used to evoke immunological effector mechanisms activated by cellular immunogens such as therapeutic vaccines, in particular to evoke specific cytotoxic T lymphocytes (CTLs) directed against target antigens. Such CTLs can exert a beneficial effect by tending to recognise and destroy tumor cells, and can also be used ex-vivo in a variety of diagnostic and/or therapeutic methods.

Where there are antigenic differences between tumor cells and normal cells, they can be recognised by the immune system, provided that the tumor-specific antigens are available in the correct form to stimulate an immune response. This avoids the need to identify tumor specific markers.

CTLs destroy cells on the basis of antigen recognition in conjunction with host major histocompatibility complex (MHC) antigens; peptides generated from the antigenic target within the cytoplasm of the host cell form a complex with host MHC molecules and are transported to the cell surface, where they can be recognised by receptors on the surface of CTLs.

One method of using the vectors, provided by this invention, is therefore to prepare a cellular immunogen such as a vaccine from tumor material derived from one or more individuals and to administer this as an immunogen or vaccine for treatment of other subjects, e.g. patients. If a CTL response against the tumor cells is desired, however, for the reasons outlined above, the target antigens should be presented in the context of the correct MHC molecules. An immunogen or vaccine prepared from a tumor of one individual may not always therefore be appropriate for another individual with a different MHC type. Since MHC molecules vary from individual to individual, it is generally necessary, in order to activate CTL responses against the target antigens, to present the relevant target antigen to the immune system in the correct MHC context. Thus for use as an immunogen such as a therapeutic vaccine, in general it is considered that the selected target antigen is best introduced into the treated subject's or patient's own cells in order to generate an appropriate CTL response.

It can therefore be especially useful to base the tumor immunogen or vaccine on a patient's own tumor cells, a procedure known as autologous vaccination. A further major advantage of this way of use is that it can take advantage of antigenic targets that may be unique to a particular tumor; it is considered that the deregulated cell cycle control that is the basis of tumor growth can, over a period of time, lead to the accumulation of genetic changes manifested as new antigenic determinants. In this connection, the last-mentioned embodiments of the present invention can avoid or solve a problem with autologous vaccination procedure, namely that autologous tumor cells are poorly immunogenic.

Procedures according to examples of the invention can involve introduction of a target gene into tumor cells removed from a subject, by laboratory procedures after which the cells so treated are reintroduced into a subject to be treated (ex-vivo treatment). An alternative procedure according to certain examples of the invention is to introduce the target gene directly into tumor cells of the patient (in vivo treatment). The advantage of an in-vivo procedure is that no laboratory manipulation of the patient's tumor cells is required. A drawback can be that effective gene transduction may be more difficult to achieve in vivo, or more difficult to achieve to a desired degree. Other, non-tumor, cells can also usefully be transfected with the virus vectors.

In a particular example, the recombinant herpesvirus is based on a disabled form of the herpes simplex virus carrying a deletion in the glycoprotein H (gH) gene, a protein present on the surface of the virus particle that is involved in entry of virus into susceptible cells. This virus can only be replicated in a producer cell line that complements the essential function missing in the viral genome: a useful example of a recombinant complementing cell line is one which has been engineered to express stably the same HSV gH gene as was deleted from the virus vector. The virus generated from the producer cell line acquires the cell-encoded gH gene product as part of its structure and is infectious. This virus preparation can infect normal cells in the same manner as wild type virus. Once in the cell, the virus genome can be intracellularly replicated, and genes carried by the genome can be expressed as protein. However the absence of a functional gH protein when the defective virus infects a normal cell results in failure to generate new infectious virus particles. The gH-deleted virus is considered to be safe to administer as a vaccine or a gene delivery vehicle.

It is preferable that a vector such as a HSV vector for cancer immunotherapy is fully disabled and unable to spread within the treated host. A useful vector can, however, be based on any HSV virus that is deemed sufficiently safe to be used in a clinical setting. It is also preferable that heterologous genes incorporated into such a gH-deleted HSV genome are inserted at the locus from which the gH gene was removed, to minimise the risk of transfer of the heterologous gene by homologous recombination to wild type HSV that might co-exist in the treated individual. The heterologous gene can however instead be inserted at any site within the virus genome.

A further adaptation of the method within the scope of the invention is to deliver the appropriate genetic material, e.g. a gene encoding an immunomodulatory protein, in the form of herpesviral amplicons packaged within herpesviral particles. Amplicon DNA is DNA that contains an origin of replication of a herpesviral genome together with DNA sequences that can direct packaging of this DNA into virus particles. Where such amplicons are present in cells along with corresponding herpesvirus (helper virus), expression of amplicon DNA can occur along with expression of herpesviral DNA. Foreign genes can be cloned into such amplicons and thus expressed in cells infected with the amplicons as well as with herpesvirus. Particles containing packaged amplicons can be phenotypically equivalent to the corresponding helper virus and hence able to infect the same host cell and are considered herein as among the defective mutant herpesvirus suitable as vectors for use in the practice of the invention. Thus virally-packaged amplicons can also be used to deliver selected DNA to desired cells. Amplicons and processes for their preparation that can be used or readily adapted for use in examples of the performance of this invention, along with further details, are described in further detail in WO 96/29421 (Efstathiou et al: Cantab Pharmaceuticals Research Ltd and Cambridge University Technical Services Ltd).

It is preferable that the HSV helper virus used for packaging the amplicons is, by itself, not harmful to the host, and so a disabled virus with an essential gene deleted, such as the gH-deleted virus described above provides an ideal helper virus as described in WO 92/05263 and other related references cited herein. Other useful helper viruses can, however, be based on herpesvirus sufficiently attenuated or disabled to be used in a clinical setting, not necessarily one that is entirely replication-defective.

The invention described here can be used to deliver chosen genetic material, e.g. DNA encoding a chosen protein such as an immunomodulatory protein, to tumor cells for the purposes of therapy. The range of genes that can be delivered for the purpose of stimulating an immune response includes genes for cytokines, immunostimulators, lymphotactin, CD40, OX40, OX40 ligand, and other genetic material mentioned herein, which can be included in the vector as single genes or multiple genes, or multiple copies of one or more genes.

In embodiments of the present invention, for example using vectors and target cells as particularly described herein below, normal and malignant human hemopoietic progenitor cells can be rapidly transduced with efficiencies ranging from 60% to 100%; the levels of transduction and gene expression that have been achieved are considered to represent high efficiency, particularly for these targets.

Embodiments of the present invention can also produce useful rapidity of expression of a transferred gene. For example under conditions as specifically described herein, positivity for expression of the transferred gene has been obtained in 80% to 100% of CD34+ cells as well as AML and ALL blasts within 24 hours after exposure to the vector. It has also been found that embodiments of the invention can provide a preparation of transduced cells that produce, and for example release, the product of the transferred gene for at least 7 days at a level proportional to the MOI (multiplicity of infection, usually reckoned in plaque-forming units (pfu)lcell), for example at MOI in the range 0.05–20, e.g. in the case of GM-CSF produced in human primary leukaemic cells by expression of the corresponding gene transferred by a gH-deletant herpesviral vector.

Accordingly, it is seen that embodiments of the present invention enable the production of immunogens, e.g. human leukaemia immunogens, in cases where the production of corresponding immunogens has presented logistic problems up to now. (Although in the case of leukaemic blasts, for example, it might be or become possible to obtain high levels of cytokine production with retroviral or adenoviral vectors in certain susceptible examples of cells, embodiments of the present invention have been found to enable consistently achievable useful high proportions of leukaemic blasts to be transduced from all patients so far tested, thus presenting useful advantage in clinical work.)

The present invention is further described below by the help of examples of procedures and products and of parts of procedures and products given by way of example only and not of limitation.

The construction of suitable vectors is illustrated non-limitatively by reference to the accompanying drawings, in which:

Figure 1:
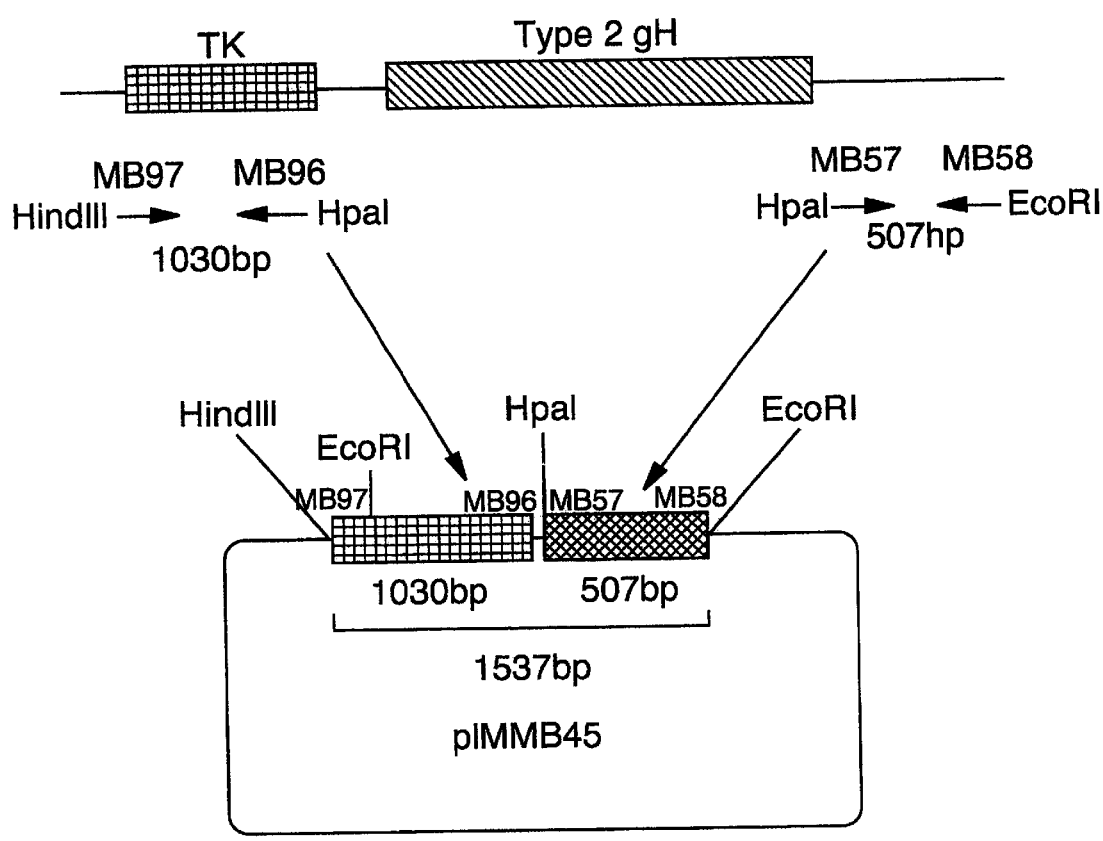
FIGS. 1 to 6 are diagrams illustrating the construction of plasmids pIMMB45, pIMMB56, pIMMB46, pIMC14, pIMR1 and pIMR3, respectively. These vectors are referred to in the description below.
Figure 2:
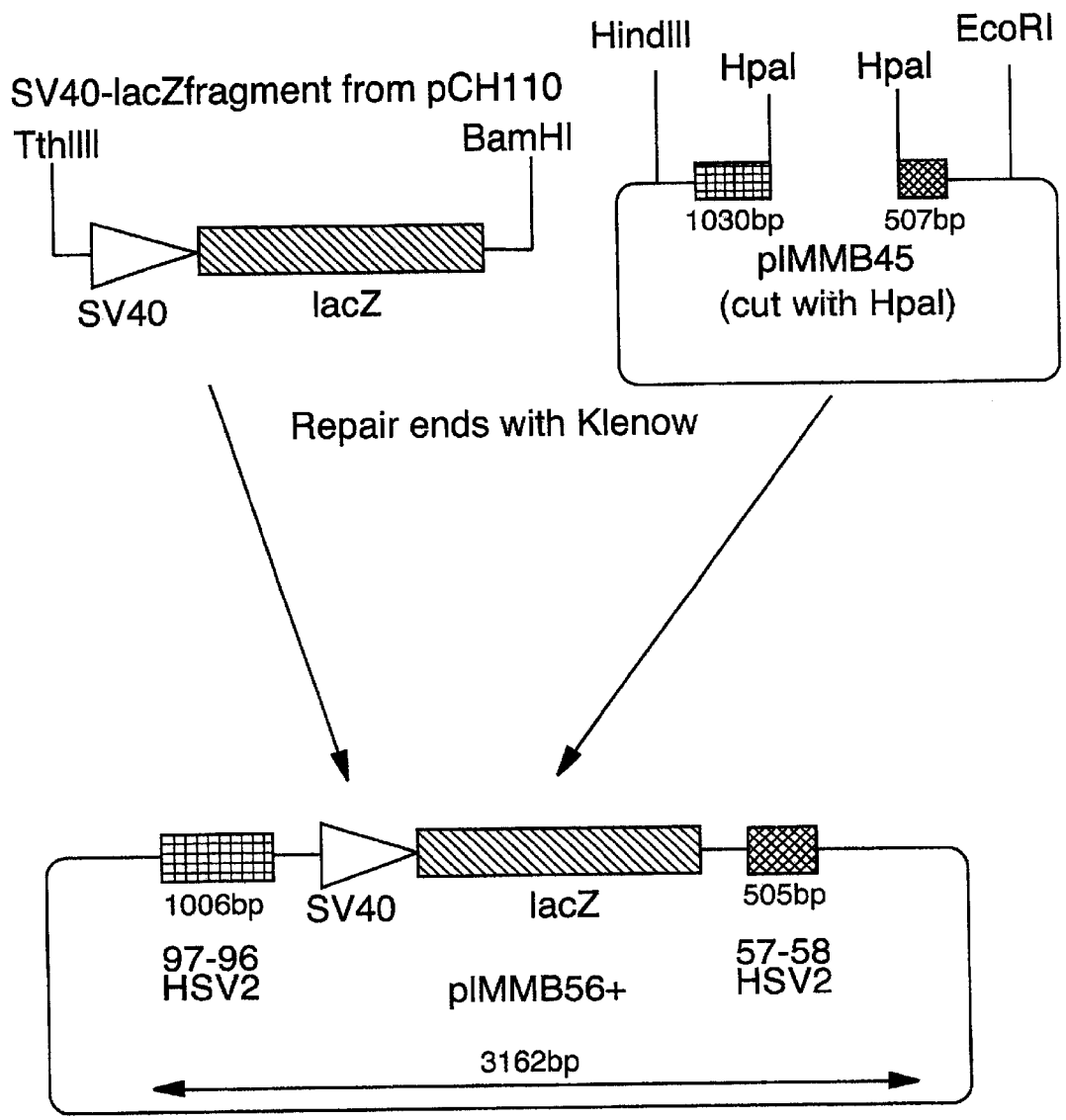
Figure 3:
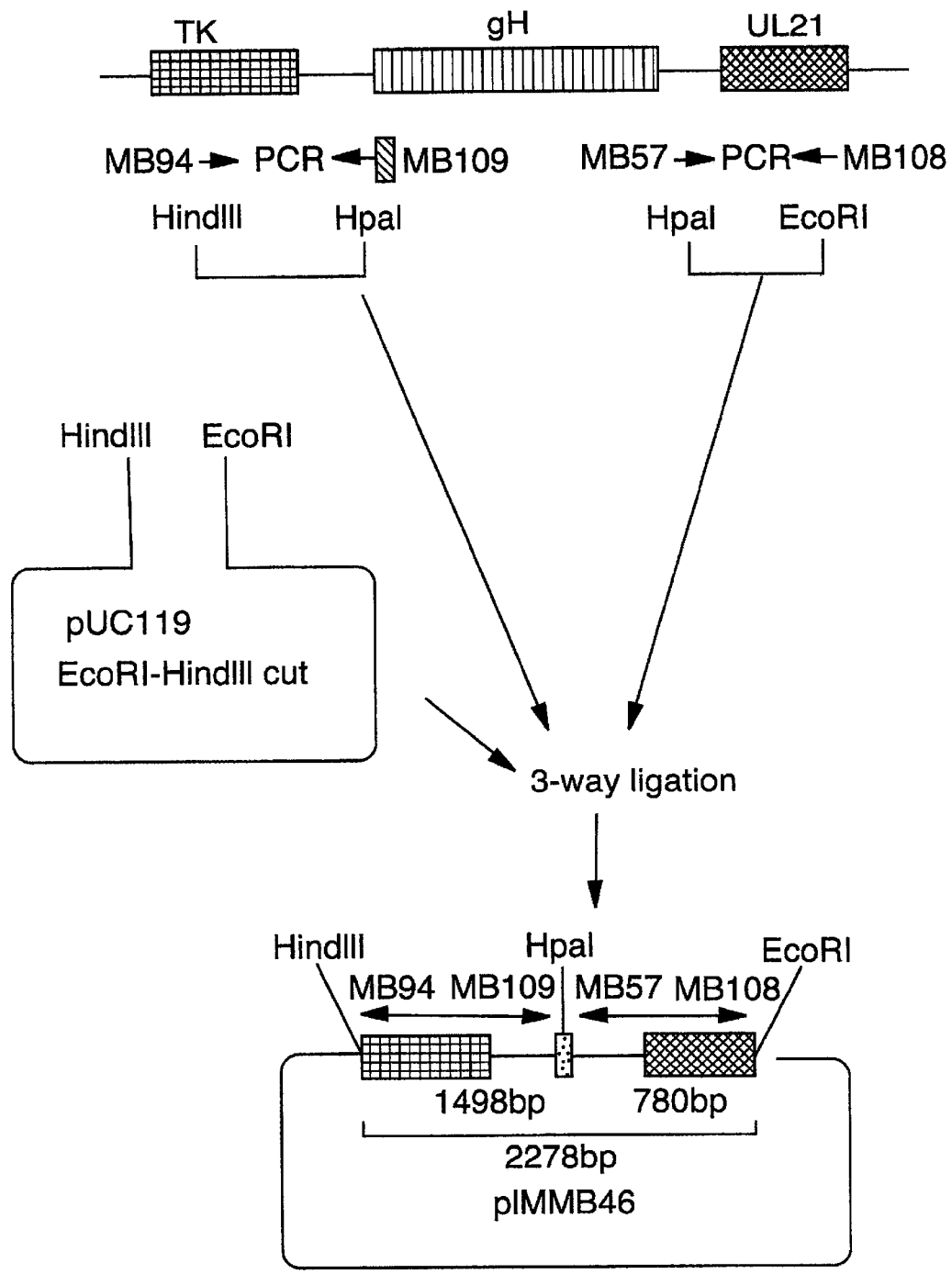
Figure 4:
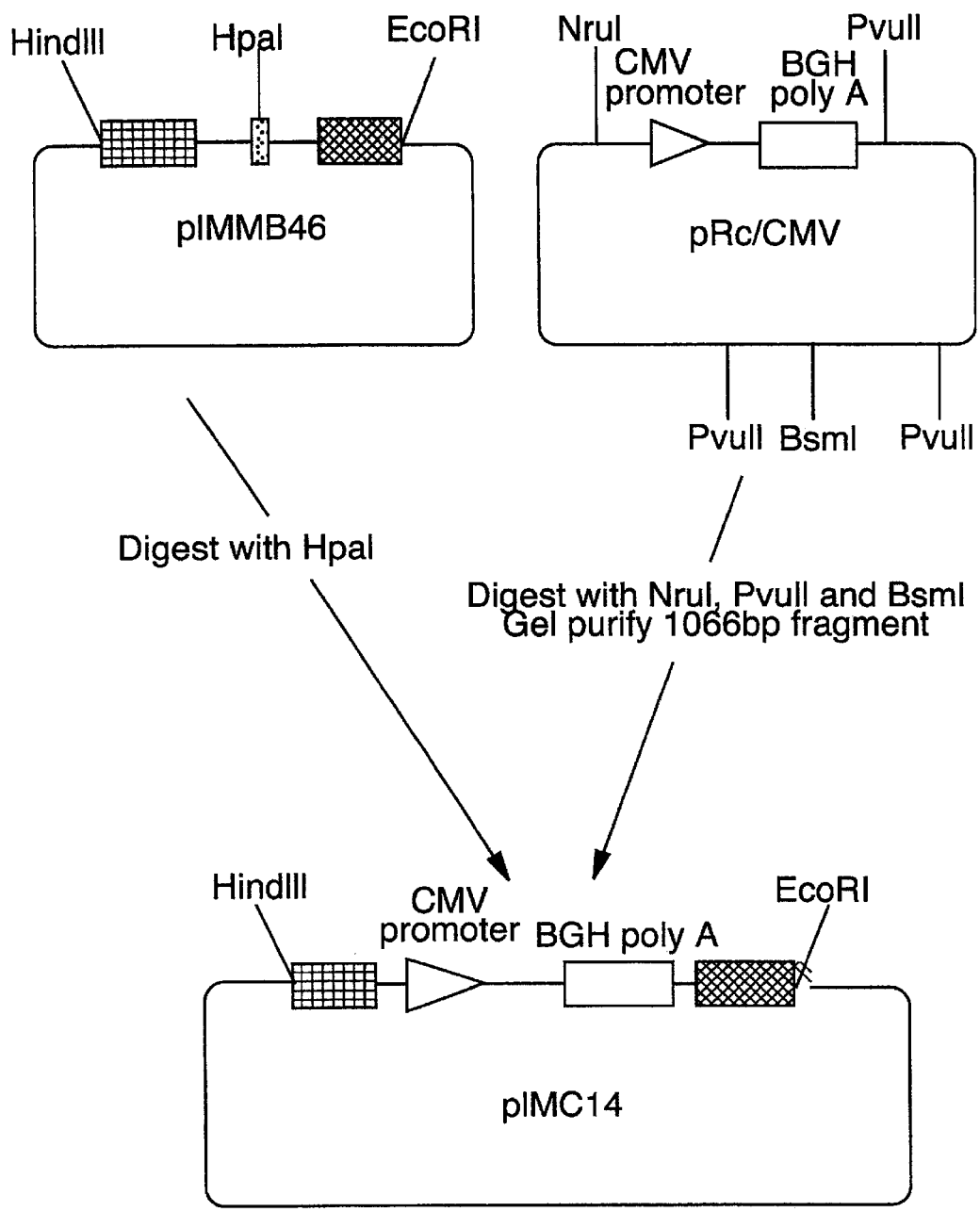

The description of vectors and their construction given below is by way of example only. The construction and properties of gH-defective virus and suitable complementing cell lines is indicated in specifications WO 92/05263 and WO 94/21807 (Cantab Pharmaceuticals Research Limited: SC Inglis et al) (hereby incorporated by reference), in Forrester et al, 1992 J. Virol. 66, pp 341 et seq, and in CS McLean et al, J Infect Dis 170 (1994) pp 1100 et seq. Further, all genetic manipulation procedures can be carried out according to standard methods as described in "Molecular Cloning" A Laboratory Manual, eds.

Sambrook, Fritsch and Maniatis, Cold Spring Harbor Laboratory Press 1989.

Delivery of the vectors into cells such as hemopoietic stem cells, and engraftment of cells into a patient to be treated therewith, can be carried out by ready adaptation of techniques per-se well-known in the field. For example, methods as indicated in MK Brenner et al, Cold Spring Harbor Symposia in Quantitative Biology, vol LIX (1994), pp 691–697, or in references cited therein, or in MK Brenner et al, Lancet 342 (6 Nov 1993) pp 1134–1137, or in references cited therein, can be readily applied and adapted.

Construction of gH-deleted HSV1 and qH-deleted HSV2 expressing GM-CSF

The gH-deleted HSV1 virus and gH-deleted HSV2 virus are propagated in the complementing cell lines. These cell lines have been engineered to express the HSV-1 gH gene or the HSV-2 gH gene respectively. Such cell lines can be constructed as described in W094/05207 and W094/21807 and references cited therein. The following section provides a further description of the construction of suitable cell lines, and starts with the construction of certain plasmids. Source of virus DNA:

Where HSV viral DNA is required, it can be made for example (in the case of HSV2) from the strain HG52 by the method of Walboomers and Ter Schegget (1976) Virology 74, 256–258, or by suitable adaptations of that method. An elite stock of the HG52 strain is kept at the Institute of Virology, MRC Virology Unit, Church Street, Glasgow, Scotland, UK. The DNA of other HSV-2 strains is likely to be very similar in this region, and strains G and MS for example can be obtained from the ATCC, Rockville, Md., USA.

Construction of Plasmid pIMC05

A 4.3kb Sst-1 fragment encoding the HSV-1 (HFEM) gH gene and upstream HSV-1 gD promoter (–392 to +11) was excised from the plasmid pgDBrgH (Forrester et al., op. cit.), and cloned into pUC119 (Vieira & Messing, 1987) to produce plasmid pUC119gH. A Not 1 site was introduced into plasmid pUC119gH by site-directed mutagenesis, 87 bp downstream of the gH stop codon. The resulting plasmid, pIMC03, was used to generate a Not 1-Sst 1 fragment which was repaired and ligated into the eucaryotic expression vector pRc/CMV (Invitrogen Corporation), pre-digested with Not 1 and Nru 1 to remove the CMV IE promoter. The resulting plasmid, pIMC05, contains the HSV-1 gH gene under the transcriptional control of the virus inducible gD promoter and BGH (Bovine Growth Hormone) poly A. It also contains the neomycin resistance gene for selection of G418 resistant stable cell lines.

Construction of gH-deleted HSV-1 Complementing Cell Line

The plasmid pIMC05 was transfected into Vero (ATCC no. 88020401) cells using the calcium phosphate technique (Sambrook, Fritsch & Maniatis, A Laboratory Manual, Cold Spring Harbor Laboratory Press 1989). Cells were selected by dilution cloning in the presence of G418 and a clonal cell line was isolated. Following expansion and freezing, cells were seeded into 24 well plates and tested for their ability to support the growth of gH-negative virus, by infection with SC16 (del)gH (Forrester et al, op. cit) at 0.1 pfu/cell. Virus plaques were observed 3 days post infection confirming expression of the gH gene.

Construction of BHK TK—cell Line

These cells were produced by transfection of plasmid pIMC05 into thymidine kinase negative (TK-) BHK cells (ECACC No. 85011423) in the same manner as that described for gH-deleted HSV-1 and gH-deleted HSV-2 complementary cells.

Construction of Plasmid PIMC08

Plasmid pIMMB24 containing the HSV-2 gH gene is constructed from two adjacent BamHI fragments of HSV-2 strain 25766. The plasmids are designated pTW49, containing the approximately 3484 base pair BamHI R fragment, and pTW54, containing the approximately 3311 base pair BamHI S fragment, both cloned into the BamHI site of pBR322. Equivalent plasmids can be cloned easily from many available strains or clinical isolates of HSV-2. The 5' end of the HSV-2 gene is excised from pTW54 using BamHI and Kpnl, to produce a 2620 base pair fragment which is gel-purified. The 3' end of the HSV-2 gH gene is excised from pTW49 using BamHI and Sall, to produce a 870 base pair fragment which is also gel-purified. The two fragments are cloned into pUC119 which had been digested with SalHI and Kpnl. This plasmid now contains the entire HSV-2 gH gene.

Plasmid pIMC08 containing the HSV-2 (strain 25766) gH gene was constructed as follows. Plasmid pIMMB24 was digested with Ncol and BstXI and the fragment containing the central portion of the gH gene was purified from an agarose gel. The 5' end of the gene was reconstructed from two oligonucleotides CE39 and CE40 which form a linking sequence bounded by HindIII and Ncol sites.

The 3' end of the gene was reconstructed from two oligonucleotides CE37 and CE38 which form a linking sequence bounded by BstXI and Notl sites.

CE39 5' AGCTTAGTACTGACGAC 3' (SEQ ID NO: 1)

CE40 5° CATGGTCGTCAGTACTA 3' (SEQ ID NO: 2)

CE37 5' GTGGAGACGCGAATAATCGCGAGC 3' (SEQ ID NO: 3)

CE38 5' GGCCGCTCGCGATTATTCGCGTCTCCA-CAAAA 3' (SEQ ID NO: 4)

The two oligonucleotide linkers and the purified Ncol-BstXI gH fragment were cloned in a triple ligation into HindIII-Noti digested pIMC05, thus replacing the HSV-1 gH gene by the HSV-2 gH gene. The resultant plasmid was designated pIMC08.

Construction of gH-deleted HSV-2 Complementary Cell Line (CR2)

The plasmid pIMCO8, contains the HSV-2 gH gene under the transcriptional control of the virus inducible gD promoter and BGH (Bovine Growth Hormone) poly A. It also contains the neomycin resistance gene for selection of G418 resistant stable cell lines. The plasmid pIMC08 was transfected into Vero (ATCC no. 88020401) cells using the calcium phosphate technique (Sambrook, Fritsch & Maniatis, A Laboratory Manual, Cold Spring Harbor Laboratory Press, 1989). Cells were selected by dilution cloning in the presence of G418 and a clonal cell line was isolated. Following expansion and freezing, these cells, designated CR2 cells, were seeded into 24 well plates, and infected with the gH deleted HSV-1 (SC16 (del)gH) at 0.1 pfu/cell. Virus plaques were observed 3 days post infection confirming expression of the gH gene.

Construction of Recombination Dilasmids a) pIMMB56+ pIMMB56 + is a vector with a lacZ cassette flanked by HSV-2 sequences from either side of the gH gene. It is made as follows: the two PCR fragments made by oligos MB97-MB96 and by oligos MB57-MB58 are digested with the restriction enzymes appropriate to the sites that have been included in the PCR oligonucleotides. The MB97-MB96 fragment is digested with HindIII and Hpal.

The MB57-MB58 fragment is digested with Hpal and EcoRI. These fragments are then ligated into the vector pUC119 which has been digested with HindIII and EcoRI. The resultant plasmid is called pIMMB45 (FIG. 1).

The oligonucleotides used for PCR are shown below:

HindIII

MB97: 5' TCGAAGCTTCAGGGAGTGGCGCAGC 3' (SEQ ID NO: 5)

Hpal

MB96: 5' TCA GTTAACGGACAGCATGGCCAGGTCAAG 3' (SEQ ID NO: 6)

Hpal

MB57: 5' TCAGTTAACGCCTCTGTTCCTTTCCCTTC 3' (SEQ ID NO: 7)

EcoRI

MB58: 5' TCA GAATTCGAGCAGCTCCTCATGTTCGAC3' (SEQ ID NO: 8)

To allow for easy detection of the first stage recombinants, the *E. coli* beta-galactosidase gene, under the control of an SV40 promoter, is inserted into pIMMB45. The SV40 promoter plus beta-galactosidase gene is excised from the plasmid pCH110 (Pharmacia) using BamHI and Tth III 1. The ends are filled in using the Kienow fragment of DNA polymerase. The fragment is gel-purified. The plasmid pIMMB45 is digested with Hpal, phosphatased with Calf Intestinal Alkaline Phosphatase (CIAP) to abolish self ligation, and gel-purified. The gel-purified fragments are then ligated together to produce the plasmid pIMMB56 + (see FIG. 2).

b) pIMMB46 pIMMB46 contains sequences flanking the HSV-2 gH gene, with a central unique Hpal site. Any gene cloned into this site can be inserted by recombination into the HSV-2 genome at the gH locus. If the virus is a TK-negative gH-negative virus, (for example made using the pIMMB56+ plasmid described above) then the plasmid will replace the 3' end of the TK gene, thus restoring TK activity and allowing selection for TK-positive virus.

The two PCR fragments made by oligos MB94-MB109 and by oligos MB57-MB108 are digested with the restriction enzymes appropriate to the sites that have been included in the PCR oligonucleotides. The MB94-MB109 fragment is digested with HindIII and Hpal. The MB57-MB108 fragment is digested with Hpal and EcoRI. These fragments are then ligated into the vector pUC 119 which has been digested with HindIII and EcoRI. The resultant plasmid is called pIMMB46 (see FIG. 3). The oligonucleotides used are as follows:

Hpal

MB57: 5' TCAGTTAACGCCTCTGTTCCTTTCCCTTC 3' (SEQ ID NO: 9)

EcoRI

MB108: 5' TCA GAATTCGTTCCGGGAGCAGGCGTGGA 3' (SEQ ID NO: 10)

HindIII

MB94: 5' TCA AAGCTTATGGCTTCTCACGCCGGCCAA 3' (SEQ ID NO: 11)

Hpal

MB109: 5' TCA GTTAACTGCACTAGTTTTAATTAATACGTATG 3' (SEQ ID NO: 12)

c) pIMC14

The plasmid pRc/CMV (Invitrogen Corporation) was digested with the restriction enzymes Nrul, Pvull and BsmI and a 1066 base pair Nrul-Pvull fragment was isolated from an agarose gel. The fragment was cloned into Hpal digested pIMMB46 (see FIG. 4). The resultant is named pIMC14.

The pRc/CMV fragment contains the cytomegalovirus major immediate early promoter (CMV-IE promoter) and the bovine growth hormone (BGH) poly A addition site. This plasmid, pIMC14, is a general recombinant plasmid with unique sites for the insertion of foreign genes which can then be recombined into an HSV-2 gH-deleted DISC vector.

d) pIMR1

Figure 5:
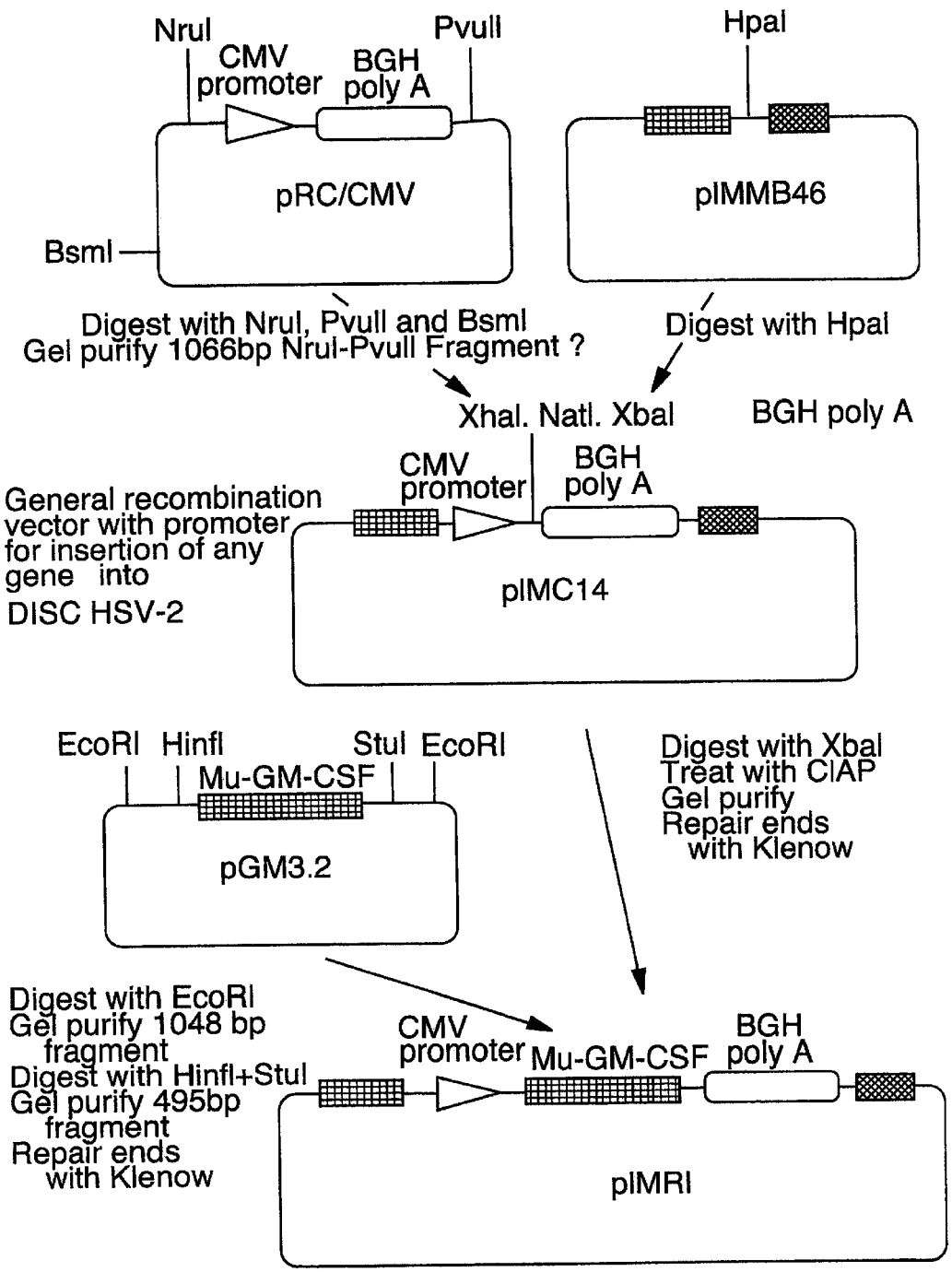
Figure 6:
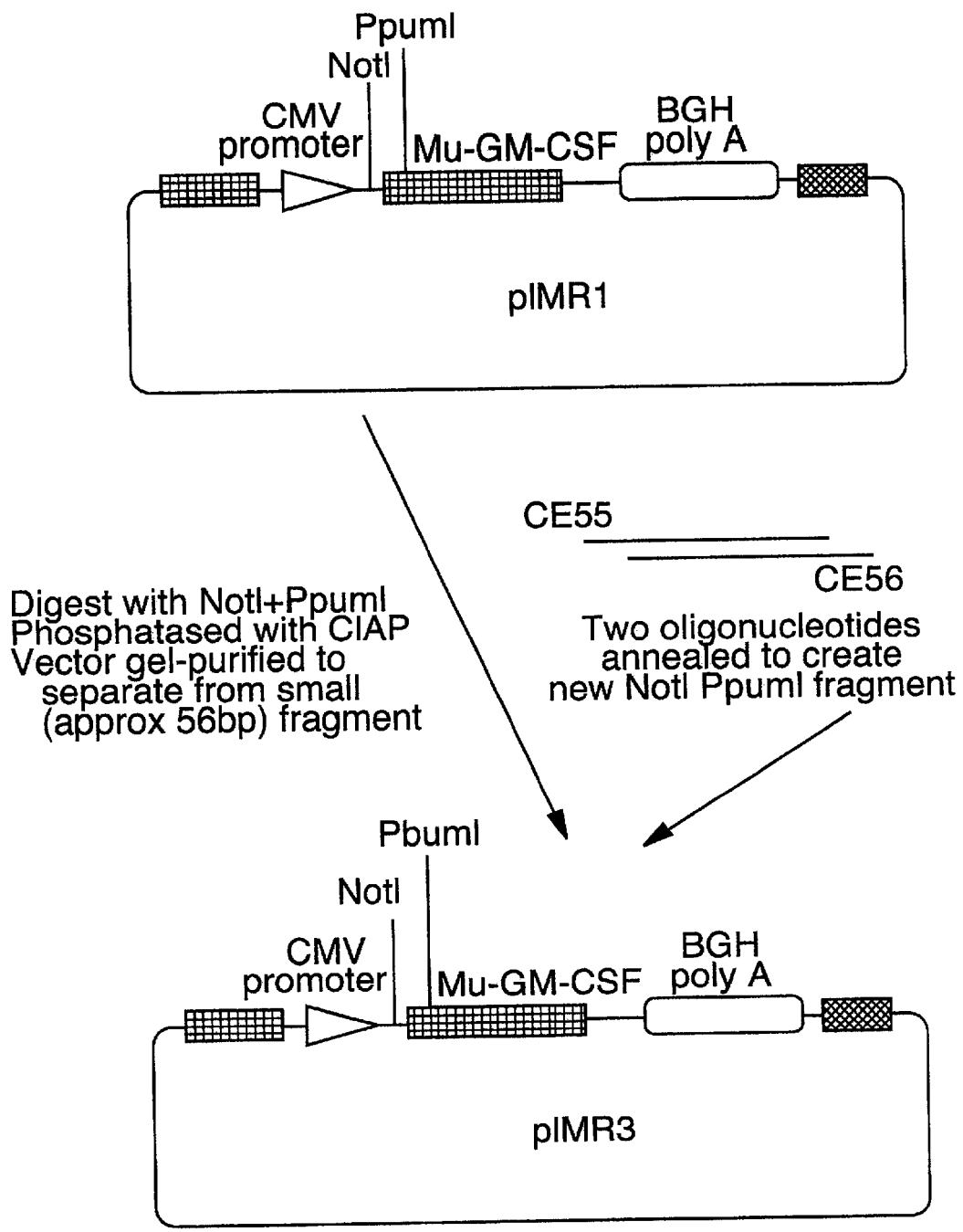

The plasmid pIMR1 is a recombination vector for the insertion of the murine GM-CSF gene, under the control of the CMV-IE promoter, into a DISC HSV-2 vector. pIMC14 is digested with XbaI, phosphatased with CIAP, gel purified and the overhanging ends made flush with Klenow polymerase. The murine GM-CSF gene is excised from the plasmid pGM 3.2FF (referred to as pGM3.2 in Gough et al. EMBO Journal 4, 645–653, 1985) (or from the equivalent plasmid constructed as described below), by a two stage procedure. Firstly pGM 3.2FF is digested with EcoRI and a 1048 base pair fragment is gel-purified. This fragment is then digested with HinfI and StuI. The 495 base pair fragment is gel-purified and the ends repaired with Klenow polymerase. This fragment is then cloned into multi cloning site of pIMC14, prepared as described above. The resulting plasmid is designated pIMR1 (see FIG. 5).

An alternative plasmid equivalent to pGM3.2, can be constructed as follows.

A library of cDNA clones is constructed from a cloned T-lymphocyte line (from a BALB/c strain of mouse), such as LB3 (Kelso et al, J Immunol. 132, 2932, 1984) in which the synthesis of GM-CSF is inducible by concanavalin A. The library is searched by colony hybridisation with a sequence specific to the murine GM-CSF gene (see Gough et al, EMBO J, 4, 645, 1985 for sequence). A example of an oligonucleotide usable in this case is 5' TGGATGACAT GCCTGTCACA TTGAATGAAG AGGTAGAAGT 3'(SEQ ID NO: 13). Clones of over 1 kb are picked and sequenced to check that they are GM-CSF. These operations can be carried out as described in "Molecular Cloning: A Laboratory Manual", by Sambrook, Fritsch and Maniatis, Cold Spring Harbor. Such an operation results in a clone containing the complete GM-CSF sequence which can be excised with HinfI and StuI as described for pGM3.2.

e) pIMR3

In the plasmid pIMR1 the open reading frame for the GM-CSF gene is preceded by a short open reading frame (ORF) of 15 base pairs. Because it is possible that this might interfere with the expression of GM-CSF, the plasmid pIMR1 was altered so that this small reading frame was removed. pIMR1 was digested with NotI and PpuMI. The digested vector was phosphatased with calf intestinal alkaline phosphatase (CIAP) and gel-purified. The sequences between the two restriction enzyme sites were replaced by a short piece of double-stranded DNA generated by the annealing of two oligonucleotides CE55 and CE56:

CE55 GGCCGCTCGAACATGGCCCAC-GAGAGAAAGGCTAAG (SEQ ID NO: 14)

CE56 GACCTTAGCCTTTCTCTCGTGGGCCAT-GTTCGAGC (SEQ ID NO: 15)

The oligonucleotides are constructed so as to have overhanging ends compatible with the NotI and PpuMI ends generated by the digestion of pIMR1. The two oligonucleotides are annealed, phosphorylated, and ligated to the NotI-PpuMI-digested pMR1. The resultant vector was designated pIMR3. The sequences in the relevant region are shown below:

```
pIMR1
TTAATACGAC TCACTATAGG GAGACCGGAA GCTTGGTACC GAGCTCGGAT    (SEQ ID NO:16)

CCACTAGTAA CGGCCGCCAG TGTGCTGGAA TTCTGCAGAT ATCCATCACA

CTGGCGGCCG CTCGAGCATG CATCTAGCCT TTTGACTACA ATGGCCACG
    NotI          Short ORF              Start of GM-CSF AGA GAAAGGCTAAGGTCCTG
               PpuMI
```

```
pIMR3
TTAATACGAC TCACTATAGG GAGACCGGAA GCTTGGTACC GAGCTCGGAT (SEQ ID NO:17)

CCACTAGTAA CGGCCGCCAG TGTGCTGGAA TTCTGCAGAT ATCCATCACA

CTGGCGGCCG CTCGAACATG GCCCACGAGA GAAAGGCTAA GGTCCTG
    Not I          Start               PpuMI
```

To make an HSV-1 DISC virus expressing the GM-CSF protein, a different set of plasmids is made:

f) pIMMB34

This is a recombination vector containing sequences flanking the HSV-1 gH gene. The left side flanking sequences inactivate TK gene which lies adjacent to the gH gene. The two PCR fragments made by oligos MB97-MB100 and by oligos MB61-MB58 are digested with the restriction enzymes appropriate to the sites that have been included in the PCR oligonucleotides. The MB97-MB100 fragment is digested with HindIII and HpaI. The MB61-MB58 fragment is digested with HpaI and EcoRI. These fragments are then ligated into the vector pUC119 which has been digested with HindIII and EcoRI. The resultant plasmid is called pIMMB34. The oligonucleotides used are as follows:

```
           HindIII                       (SEQ ID NO:18)
MB97:  5' TCGAAGCTTCAGGGAGTGGCGCAGC 3'

HpaI                          (SEQ ID NO:19)
MB100  5' TCAGTTAACGGCCAGCATAGCCAGGTCAAG 3'

HpaI                          (SEQ ID NO:20)
MB61:  5' TCAGTTAACAGCCCCTCTTTGCTTTCCCTC 3'

EcoRI                         (SEQ ID NO:21)
MB58:  5' TCAGAATTCGAGCAGCTCCTCATGTTCGAC 3'
``` g) pIMMB55 +

To allow for easy detection of the first stage recombinants, the E. coli beta-galactosidase gene, under the control of an SV40 promoter is inserted into pIMMB34. The SV40 promoter plus beta-galactosidase gene is excised from the plasmid pCH110 (Pharmacia) using BamHI and Tth III 1. The ends are filled in using the Klenow fragment of DNA polymerase. The fragment is gel-purified. The plasmid pIMMB34 is digested with Hpal, phosphatased with Calf Intestinal Alkaline Phosphatase (CIAP) to abolish self ligation, and gel-purified. The gel-purified fragments are then ligated together to produce the plasmid pIMMB55 +.

h) pIMMB63:

pIMMB63 is made from HSV-1 strain KOS (m) DNA. pIMMB63 contains sequences flanking the HSV-1 gH gene, with a central unique Hpal site. Any gene cloned into this site can be inserted by recombination into the HSV-1 genome at the gH locus. If the virus is a TK-negative virus (for example made using the pIMMB55 + plasmid described above) then the plasmid will replace the 3' end of the TK gene, thus restoring TK activity and allowing selection for TK-positive virus.

The two PCR fragments made by oligos MB98-MB63 and by oligos MB61-MB58 are digested with the restriction enzymes appropriate to the sites that have been included in the PCR oligonucleotides. The MB98-MB63 fragment is digested with HindIII and Hpal. The MB61-MB58 fragment is digested with Hpal and EcoRI. These fragments are then ligated into the vector pUC119 which has been digested with HindIII and EcoRI. The resultant plasmid is called pIMMB63. The oligonucleotides used are as follows:

```
         HindIII                         (SEQ ID NO:22)
MB98: 5' TCAAAGCTTATGGCTTCGTACCCCTGCCAT 3'

HpaI                            (SEQ ID NO:23)
MB63: 5' TCAGTTAACGGACCCCGTCCCTAACCCACG 3'

HpaI                            (SEQ ID NO:24)
MB61: 5' TCAGTTAACAGCCCCTCTTTGCTTTCCCTC 3'

EcoRI                           (SEQ ID NO:25)
MB58: 5' TCAGAATTCGAGCAGCTCCTCATGTTCGAC 3'
``` i) pIMX1.0

This plasmid is a general recombination plasmid with unique sites for the insertion of foreign genes which can then be recombined into an HSV-1 gH-deleted DISC vector. The plasmid pRc/CMV was digested with NruI and PvuII and a 1066 bp fragment, which contains CMV IE promoter and a polyA signal, was blunt ended with Klenow polymerase and inserted into the unique Hpal site of plasmid pIMMB63. This plasmid is named pIMX1.0. The multiple cloning site contained between the CMV IE promoter and the polyA signal is ideal for cloning other genes into the plasmid and their subsequent introduction into DISC HSV-1.

j) pIMX3.0

The plasmid pIMX3.0 is a recombination vector for the insertion of murine GM-CSF, under the control of CMV IE promoter, into the deleted gH region of type I DISC HSV. This plasmid was constructed by inserting the murine GM-CSF which was excised out from plasmid pGM3.2FF (op. cit.) with SmaI and DraI, into the unique BsaBI site of pIMX1.0. This plasmid, pIMX3.0, is the HSV-1 equivalent of pIMR3.

Construction of Recombinant Virus

Recombinant virus expressing GM-CSF was made in two stages. In the first stage the gH gene, and part of the TK gene are replaced by a "lacZ cassette", consisting of the SV40 promoter driving the *E. coli* lacZ gene. This virus has a TK minus phenotype and also gives blue plaques when grown under an overlay containing the colourigenic substrate X-gal. This recombinant virus can now be conveniently used for the insertion of foreign genes at the gH locus. Genes are inserted in conjunction with the missing part of the TK gene. At the same time the lacZ cassette is removed. These viruses can be selected on the basis of a TK-positive phenotype, and a white colour under X-gal.

a) Construction of First Stage Recombinant with SV40-lacZ Cassette Replacing gH.

Recombinant virus was constructed by transfection of viral DNA with the plasmid pIMMB56+ (for HSV-2) or pIMMB55+ (for HSV-1). Viral DNA is purified on a sodium iodide gradient as described in Walboomers & Ter Schegget (1976) Virology 74, 256–258.

Recombination is carried out as follows:

a) First Stage

A transfection mix is prepared by mixing 5 μg of viral DNA, 0.5 μg of linearised plasmid DNA (linearised by digestion with the restriction enzyme ScaI) in 1 ml of HEBS buffer (137 mM NaCl, 5 mM KCl, 0.7 mM $Na_2HPO_4$, 5.5 mM glucose, 20 mM Hepes, pH 7.05). 70 μl of 2M $CaCl_2$ is added dropwise, and mixed gently. The medium is removed from a sub-confluent 5 cm dish of CR1 or CR2 cells (gH-expressing Vero cells) and 500 μl of the transfection mix is added to each of two dishes. The cells are incubated at 37° C. for 40 minutes, when 4 ml of growth medium containing 5% foetal calf serum (FCS) are added. 4 hours after adding the transfection mix, the medium is removed and the cells washed with serum-free medium. The cells are then 'shocked' with 500 μl per dish of 15% glycerol for 2 minutes. The glycerol is removed, the cells washed twice with serum-free medium and growth medium containing 5% FCS is added.

After 4–7 days, when a full viral cytopathic effect (CPE) is observed, the cells are scraped into the medium, spun down at 2500 rpm for 5 minutes at 4° C., and resuspended in 120 μl of Eagles minimal essential medium (EMEM). This is now a crude virus stock containing wild-type and recombinant virus. The stock is frozen, thawed and sonicated and screened for recombinants on CR1 cells at a range of dilutions. The medium contains 10 μg/ml of acyclovir, to select for TK-minus virus. After addition of the virus dilutions, the cells are overlaid with medium containing 1% low-gelling temperature agarose. After the appearance of viral plaques at about 3 days, a second overlay of agarose containing 330 μg/ml of Xgal as well as 10 μg/ml acyclovir, is added. Blue plaques are picked, within 48 hours, and transferred to 24-well dishes (1 cm2 per well) containing CR1 cells. The plaques are allowed to grow to full CPE and harvested by scraping into the medium. Multiple rounds of plaque-purification are carried out until a pure stock of virus is obtained.

The structure of the first stage recombinant is confirmed as follows. Sodium iodide purified viral DNA is prepared as before, and digested with BamHI. This digest is separated on an agarose gel and transferred to a nylon membrane. This is probed with a radiolabelled DNA fragment homologous to the sequences either side of the gH gene.

b) Second Stage.

Recombination is carried out as before using viral DNA from the first stage recombinant, and the plasmid pIMR3 (for HSV-2) or pIMX3.0 (for HSV-1). After the initial harvest of virus, TK-positive recombinant viruses are selected by growth on BHK gH-positive TK-negative cells, in the presence of 0.6 μM methotrexate, 15 μM Thymidine, 9.5 μM Glycine, 4.75 μM Adenosine and 4.75 μM Guanosine. Three rounds of this selection are carried out in 6-well dishes (10 $cm^2$ per well). At each stage the infected cells are harvested by scraping into the medium, spinning down and resuspending in 200 μl of EMEM. After sonication, 50 μl of this is added to fresh BHK gH-positive TK-negative cells, and the selection continued.

After the final selection the virus infected cells are harvested as before and screened on gH-deleted HSV1 complementary cells. Overlays are added as before and white plaques are selected in the presence of Xgal. Plaques are picked as before and plaque-purified three times on said gH-deleted HSV1 complementary cells.

The structure of the viral DNA is analysed as before.

GM-CSF Assay

Cos 1 cells (ECACC No. 88031701) are transfected with plasmid DNA using DEAE dextran as described in Gene Transfer and Expression, A laboratory Manual, Michael Kriegler. Supernatants from transfected Cos 1 cells or infected CR2 cells are screened for GM-CSF activity by bioassay. An IL-3/GM-CSF responsive murine hemopoietic cell line designated C2GM was obtained from Dr. E. Spooncer, Paterson Institute for Cancer Research, Christie Hospital, UK. The cell line C2GM is maintained in Fischers media with 20% horse serum, 1% glutamine and 10% conditioned cell media. The conditioned cell media is obtained from exponentially growing cultures of Wehi 3b cells (ECACC No. 86013003) which secrete murine IL-3 into the media. Wehi 3b cells are maintained in RPMI 1640 media, 10% FCS and 1% glutamine.

The above description particularly enables construction of HSV- 1 and HSV-2 mutants which are gh-negative and which express GM-CSF, etc.

The skilled person can readily adapt the present teaching to the preparation of other mutant viruses which are defective in respect of a first gene essential for the production of infectious virus, such that the virus can infect normal cells and undergo replication and expression of viral antigen in these cells but cannot produce named infectious virus and which also express a heterologous nucleotide sequence which encodes an immunomodulating protein or other genetic material as mentioned herein.

Many other mutant viruses can be made on the basis of deletion or other inactivation (for example) of the following essential genes in the following viruses and virus types:

In herpes simplex viruses, essential genes such as gB, gD, gL, ICP4, ICP8 and/or ICP27 can be deleted or otherwise inactivated as well as or instead of the gH gene used in the above examples. In other herpesvirus, known essential genes, such as any known essential homologues to the gB, gD, gL, gH, ICP4, ICP8 and/or ICP27 genes of HSV, can be selected for deletion or other inactivation. Cytomegalovirus can e.g. be genetically disabled by deleting or otherwise activating genes responsible for temperature-sensitive mutations, for example as identifiable from Dion et al, Virology 158 (1987) 228–230.

Use of the Vectors for Transduction of Cells:

A procedure which can be adapted to the production of a number of useful examples according to the present invention is as follows.

A recombinant HSV-2 virus with a deletion in the gH gene, and carrying at the locus of the deleted gene a functional copy of the chosen gene, constructed as described above, is cultured as described and stocks are prepared with a titre of approximately 10^8 pfu/ml.

To carry out the transduction procedure on leukemia cells, blood samples are obtained from leukaemia patients and cells are isolated therefrom by density gradient centrifugation. In alternative embodiments, cell lines can be derived from cancer patients by biopsy or otherwise and can be used directly or following culture in vitro. Cells from patients with solid tumors can be obtained following surgical removal of the tumor or of metastases, or from biopsy material from the tumor or metastases. Tumor biopsies or re-sected material can be used to prepare single cell suspensions either by mechanical or enzymic disaggregation or by other well known methods.

Infection/transduction of tumor cells or cell lines with the recombinant defective HSV vector carrying a gene of choice (e.g. GM-CSF) can be carried out in vitro by dispensing aliquots of a single-cell suspension into suitable tissue culture vessels such as 24-well plates or flasks. A suitable cell concentration can be 0.5 to 2.0×10^6 cells/well in 1 or 2 ml of medium. Virus can then be added at a multiplicity of infection for example in the range 0.01–20, for example 0.05 to 0.1 pfu/cell, or up to 1 or up to about 5 pfu/cell, and the culture is incubated for 2 h to allow the virus to enter the cell. Excess virus is then washed away in standard manner. The cells can be used for immunotherapeutic and other purposes as mentioned herein either directly or after culture in fresh medium for varying lengths of time, e.g. for up to 1 to 7 days. For test purposes, as in the test experiments described below, culture was carried out for 1 to 7 days.

Samples of the cells infected by the virus vector can be examined for expression of the heterologous gene carried within the virus vector. For example, cells infected with a recombinant defective HSV vector containing the lac Z gene can be tested for the presence of β-galactosidase activity either by using an antibody or antiserum preparation directed against β-galactosidase, or by using a galactosidase substrate (e.g. Fluoreporter (TM)) which upon cleavage by β-galactosidase gives a fluorescent product. The fluorescent product or antibody can then be detected by fluorescence microscopy or by flow cytometry. The proportion (%) of cells showing fluorescence, indicates the proportion expressing the gene product and can be calculated from the results of the detection step.

Transduction and Expression of Lacz in Malignant and Normal Cells:

A suitable test system to test and illustrate the effectiveness of transduction in accordance with the present invention, using a recombinant virus vector, is as follows, and can be adapted to other examples of herpesvirus vector. The vector used in the test described here contains a lacz reporter gene: generally a different vector having a gene encoding an immunomodulatory protein or other protein, or other genetic material as mentioned herein, in place of the reporter gene (or in addition to it) is used in the practice of the invention.

A lacz gh-deleted HSV mutant was constructed as described herein above, with reference to the 'first stage' mutant virus. This first stage in the production of the vector containing the gene for the immunomodulatory protein is a suitable test vector used in the test procedure described below. Alternatively, such mutants can also be constructed as described in specification WO 94/21807, corresponding with the 'first stage' recombinant mentioned in WO 94121807, construction of which is described on page 28 line 28 to page 29 line 26 with associated description (hereby incorporated by reference). The lacZ gene is used here as a test and marker gene. Using the techniques described herein and in the mentioned specifications, other useful genes can readily be incorporated in the place of the lacz or as well as the lacz gene.

The ability of the recombinant defective HSV virus vector HSV-lac Z to induce expression of the β galactosidase marker gene has been studied by way of example in the following different tumor cell types:

A: Two independent cell lines derived from acute lymphoblastic leukaemias (ALL); (AD and RS human pre-B-leukaemic cell lines established at St Jude Children's Research Hospital, Memphis, Tenn. from clinical samples and cultured in RPMI 1640 (Biowhittaker) supplemented with 10% FCS (Biowhittaker, Walkersville, Md.), 100IU/ml penicillin and 100mu-g/ml streptomycin (Biowhittaker), and 2 mmol/l L-glutamine));

B: Three independent cell lines derived from neuroblastoma (NB);

C: Primary cells freshly isolated from four patients with ALL;

D: Primary cells derived from three patients with acute myeloid leukaemia (AML); and E: Primary cells derived from two patients with NB.

Leukaemic blast cells were isolated from patients with >80% blast cells by Ficoll sedimentation of peripheral blood or bone marrow mononuclear cells. Myeloblasts can be maintained in liquid culture in RPMI supplemented as above (Biowhittaker). Lymphoblasts can be maintained in liquid culture or where necessary on allogeneic skin fibroblasts as stromal support.

Cell lines or freshly isolated cells, respectively, were plated out as single cell suspensions in 24 well plates at 5×10^5 to 2×10^6 cells/well in 1 or 2 ml of medium. The recombinant defective HSV virus vector HSV-lac Z was added at a multiplicity of 0.05 to 0.1 pfu/cell and cultures were incubated at 37 deg C for 2 h. Excess virus was removed, fresh medium added and the cultures incubated at 37 deg C for varying lengths of time. Successful transfection was determined by flow cytometry, and measurements were made on days 2 and 7 after infection. The infected cells were stained (xgal and standard fluorochrome) and checked for production of lacz.

The following results were obtained: For both of the ALL cell lines, transduction efficiency for the β-galactosidase gene carried by the vector was 100% on both days 2 and 7.

Of the primary ALL cell samples, two were 100% positive for β-galactosidase expression and the other two showed more than 80% transduction efficiency on day 2. (These cells do not survive in culture in the absence of stroma, and hence they could not be tested at day 7.)

Two of the three primary AML samples showed transduction efficiencies of more than 80%; these figures increased further by day 7.

The third sample showed a somewhat lower efficiency (42% on day 2 and 54% on day 7).

On day 2, the three NB cell lines gave 25%, 72% and 74% transduction efficiencies respectively, while the two primary NB cell samples showed 65% and 100% transduction.

These results demonstrate high capacity of the recombinant defective HSV vector for transduction of the heterologous gene into cells which previously proved difficult to transduce by other means. For ALL and AML, retrovirus transduction requires the generation of cell lines, and even then, the efficiency of gene transfer has generally been found to be very low (<5%). Fresh cells or cell lines derived from ALL and AML are considered to be essentially resistant to adenovirus transduction.

The recombinant defective HSV vector has also shown a surprisingly high capacity for transduction of fresh NB cells and NB cell lines. The transduction efficiency for two of the three NB cell lines was >70%, and for the fresh isolates it was 65% and 100% respectively.

These results are summarised as follows:

| | Day 2 | | Day 7 | |
|---|---|---|---|---|
| Cell type | % positive | % viable | % positive | % viable |
| ALL cell line - AD | 100 | 30 | 100 | 56 |
| ALL cell line - RS | 100 | 31 | 100 | 53 |
| Fresh ALL - LI | 100 | 77 | | |
| Fresh ALL - SP | 100 | 81 | | |
| Fresh ALL - BR | 91 | 87 | | |
| Fresh ALL - RU | 85 | 100 | | |
| Fresh AML - RE | 80 | 50 | 95 | 40 |
| Fresh AML - BA | 86 | 62 | 86 | 91 |
| Fresh AML - TE | 42 | 90 | 54 | 20 |
| NB cell line - MC | 72 | 100 | | |
| NB cell line - JF | 74 | 100 | | |
| NB cell line - NH | 25 | 100 | | |
| Fresh NB - RE | 65 | 100 | | |
| Fresh NB - HI | 100 | ND | | |

Transduction and expression of lac in primary bone marrow cells was carried out as follows:

Bone marrow was obtained from two normal donors. The mononuclear fraction (by Ficoll sedimentation) was passed down an anti-CD34 column (Cellpro, Seattle, Wash.) to enrich the CD34+ progenitor cell population. These cells were then exposed to the lacz-encoding disabled herpesvirus described above at a number of different multiplicities of infection MOI), ranging from 0.05–20 (pfu/cell). After 2 hours exposure, the cells were divided into two portions and could be maintained either in stromal support cultures or in culture with cytokines as mentioned below. The stromal support cultures with 8×10^5/sq.cm of surface area were established in Fisher's medium (Life Technologies, Grand Island, N.Y.), with 15% horse serum and 5% fetal calf serum (FCS: Summit Biotechnology, Ft Collins, Colo.), 1×10^6mol/l hydrocortisone (Abbott, Chicago, Ill.), 10^4 mol/l mercaptoethanol (Sigma, St Louis, Mo.) and 400 mu-l/ml transferrin (Life Technologies). Cells were cultured in 25-ml tissue culture flasks (Nunc, Roskilde, DK) at 37 deg.C. Every 2 weeks half of the spent medium was replaced by fresh medium until the stromal layer was fully established. Stromal cells were then employed as feeder layers and reseeded with transduced CD34+ cells obtained as described above. An alternative culture method for a portion of the transduced cells is to grow them in liquid media supplemented with foetal bovine serum, IL3 and stem cell factor. The other of the portions was mixed in methylcellulose and grown in tissue culture dishes at a density of 10^5/ml.

After 2, 7 and 14 days, cells from the liquid culture were analyzed by flow cytometry (using the Fluoreporter system), while cells from the methylcellulose plates were examined by x-gal staining of individual colonies and by fluorescence flow cytometry. In the fluorescence studies, all cells were dual stained with the Fluoreporter reagent and with fluorescent anti-CD34 antibody.

The results showed that 30–100% of CD34+ cells were positive for the marker gene, with the proportion of positive cells increasing as the MOI increased. By day 14, a smaller proportion of the cells and colonies were positive (2–50%), implying that expression of the transferred gene was transient in some cells. Since cells and individual colonies in semisolid (methylcellulose) cultures were also positive, while the methylcellulose itself is fluorescence negative, the signal detected is not due to exchange of protein from transduced cells to non-transduced cells, but represents highly efficient transduction of normal hemopoietic progenitor cells, in the absence of any growth stimulatory signals. In further tests, it was found that high-efficiency of expression was obtainable at for example 48 hours after transduction, reaching a peak by about 24 to 48 hours.

The methods described above for transduction and expression of lacz are readily adaptable to the expression of other desired proteins and genetic material by the use of alternative virus vectors carrying corresponding other genetic material in place of lacz as described above.

Expression of GM-CSF by Vector-transformed Human ALL and Other Cells:

Data have been obtained, showing that an example of a disabled herpesviral vector carrying a gene encoding a cytokine (GM-CSF) (gH-deletant HSV vector encoding GM-CSF), constructed as described above, can induce production of the encoded cytokine in transduced cells of human acute lymphocytic leukaemia (ALL), as well as in murine lymphoblastic leukaemia (MLL) and human neuroblastoma cell lines.

Figure 7:
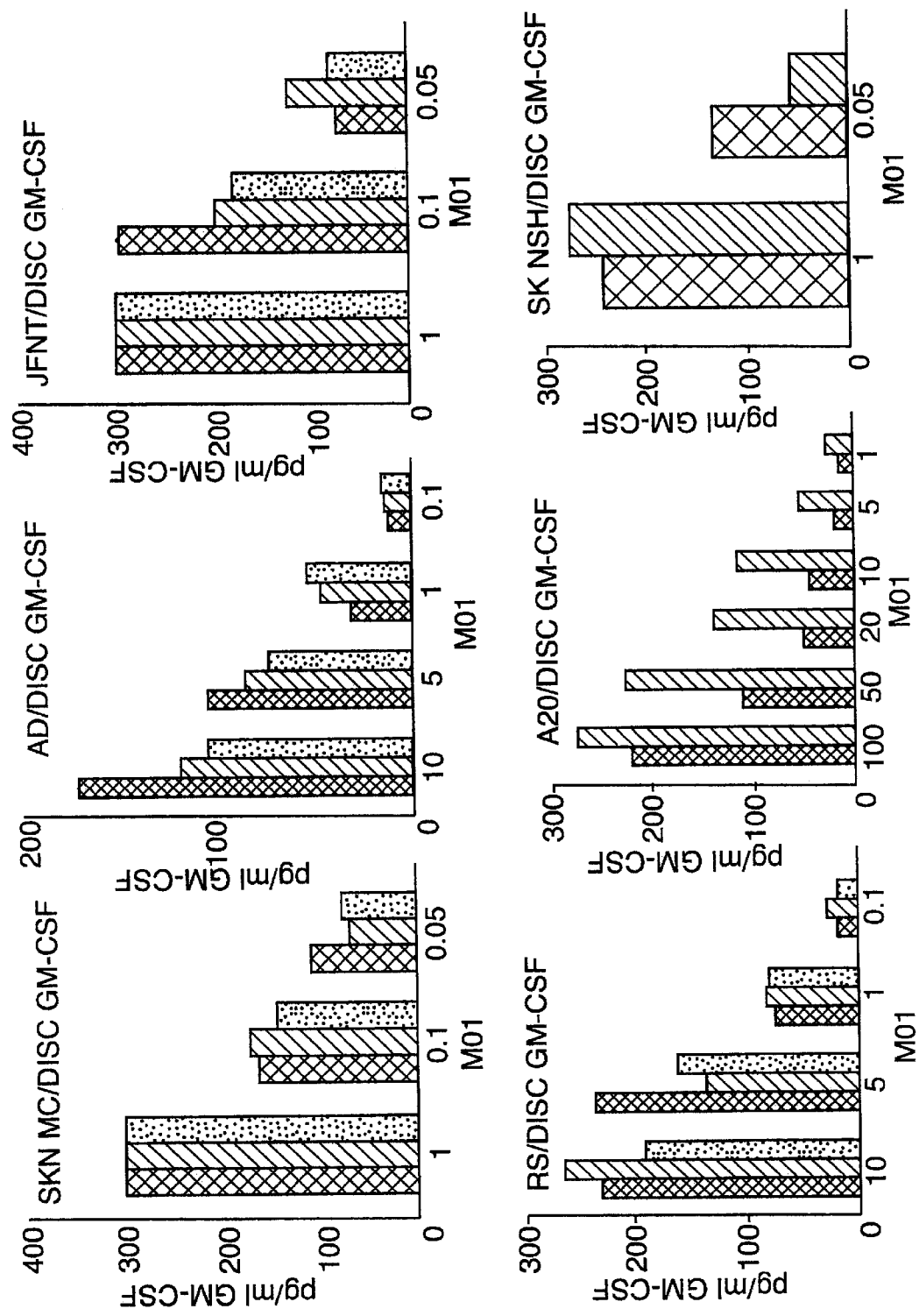
FIGS. 7 and 8 show results of transducing cells, in accordance with particular embodiments of the invention, with genetically disabled herpesvirus constructed as described below.

Cell lines were transduced in standard manner, and at days 1, 3 and 7 after transduction, they were tested for GM-CSF secretion by a commercially-available immunoassay (Endogen). FIG. 7 shows bar charts expressing results of tests for GM-CSF secretion by different transduced cell lines at different MOI (multiplicity of infection: ratio of viral pfu to cell count). The contiguous bars in each set of three refer to the production at 1, 3 and 7 days respectively under a given indicated set of conditions (cell type, MOI). The vertical axis indicates scale of GM-CSF production per $5 \times 10^5$ cells per 24 hours.

Secretion has been seen to occur for at least 7 days, and the results appear not to be due merely to persistence of protein expressed earlier. Low multiplicities of infection (e.g. in the range from about 0.05 to about 1, 5 or 10) can thus be effective for human tumor cells. Mouse tumor cells, used for comparison, were about 20-fold less readily transduced than human cells.

Figure 8:
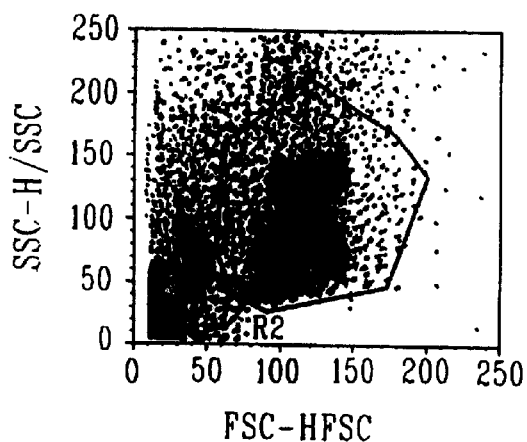
Figure 8:
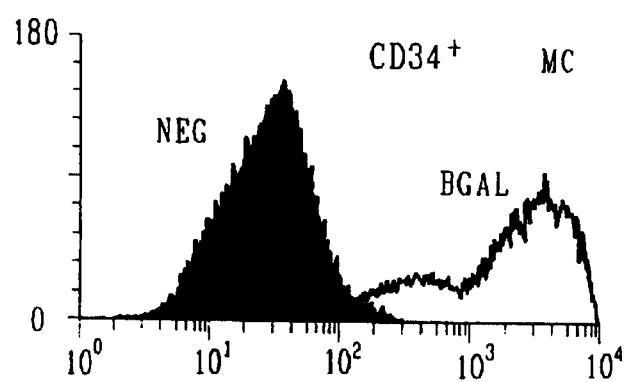
Figure 8:
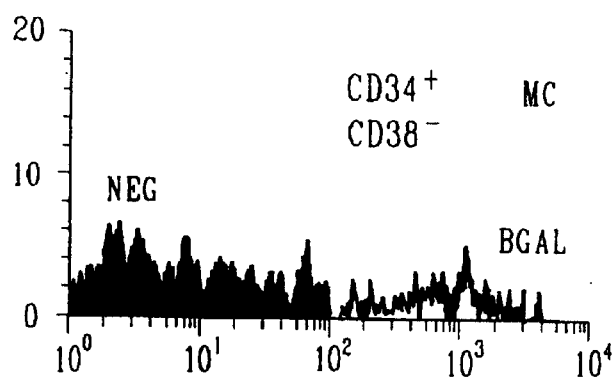

Expression of GM-CSF by CD34+ Primary Bone Marrow Cells:

FIG. 8 is a FACS plot showing the result of a successful transduction of CD34+ primary bone marrow cells (hemopoietic progenitor cells) from a normal adult human source.

Bone marrow cells were transformed using the disabled herpesviral vector carrying a gene encoding a cytokine (GM-CSF) (gH-deletant HSV vector encoding GM-CSF). The cells were purified in standard manner by CD34 selection and stained in standard manner for CD34 antigen. In a similar way, other CD34 cells, e.g. those showing malignant properties, can be transduced and thereafter used, e.g. reinfused as immunogenic therapeutic vaccine into the patient from whom the parental cells were derived, or used in-vitro/ex-vivo to prime or stimulate lymphocytes.

The examples and embodiments described herein are for illustration and not limitation: variations and modifications will be apparent in the light of this description to persons skilled in the field, and are included within the scope of the invention. This disclosure and invention extend to combinations and subcombinations of the features mentioned, and the present disclosure includes the documents cited herein, which are hereby incorporated by reference.

We claim:

1. A method of introducing a heterologous nucleic acid sequence into cells comprising:
   transducing said cells with a mutant non-transforming herpesvirus vector comprising said heterologous nucleic acid sequence, wherein said mutant non-transforming herpesvirus vector is deleted for a gene essential for the production of infectious virus such that said mutant non-transforming herpesvirus can infect normal host cells and undergo replication and expression of viral genes in said normal host cells but cannot produce infectious virus, and wherein the cells that are transduced are selected from the group consisting of: hemopoietic cells, malignant cells of hemopoietic lineage, and malignant or non-malignant CD34+ cells.

2. The method of claim 1, wherein the heterologous nucleic acid sequence encodes an immunomodulatory protein.

3. The method of claim 1, wherein the cells that are transduced are selected from the group consisting of: cells that prior to transduction have not been incubated at all under cell culture conditions, cells that have not been incubated for more than about 2 hours under cell culture conditions, cells that have not been incubated for more than about 4 hours under cell culture conditions, and cells that have not been incubated as long as overnight under cell culture conditions.

4. The method of claim 1, further comprising contacting the transduced cells with leukocytes in vitro.

5. The method of claim 1, wherein the cells that are transduced are treated ex vivo and wherein said transducing is carried out with an efficiency of transduction of at least 42%.

6. The method of claim 1, wherein the cells that are transduced are treated ex-vivo and wherein said transducing is carried out with an efficiency of transduction of at least 65%.

7. The method of claim 1, wherein the cells that are transduced are treated ex-vivo and wherein said transducing is carried out with an efficiency of transduction of more tan 80%.

8. The method of claim 1, wherein the cells that are transduced are transduced ex-vivo at a multiplicity of infection from 0.05 to 20.

9. The method of claim 1, wherein said heterologous nucleic acid sequence is in the genome of the mutant non-transforming herpesvirus vector at the site of said gene.

10. The method of claim 1 wherein said mutant non-transforming herpesvirus is a mutant of HSV.

11. The method of claim 2, wherein the immunomodulatory protein is a cytokine, an immunological co-stimulatory molecule, or an immunological chemo-attractant.

12. The method of claim 1, wherein said heterologous nucleic acid sequence encodes a cytokine selected from the group consisting of GMCSF, IL2, IL12, CD40L, B7.1, and lymphotactin.

13. The method of claim 1, wherein the transduction is in vitro.

14. The method of claim 1, wherein the transduction is ex vivo.

15. The method of claim 1, wherein the cells that are transduced are transduced in vitro to produce transduced cells, and wherein the method further comprises infusing said transduced cells into a subject.

16. The method of claim 15, wherein the transduced cells are isolated from said subject.

* * * * *

UNITED STATES PATENT AND TRADEMARK OFFICE
CERTIFICATE OF CORRECTION

PATENT NO.     : 6,344,445 B1
DATED          : February 5, 2002
INVENTOR(S)    : Boursnell et al.

It is certified that error appears in the above-identified patent and that said Letters Patent is hereby corrected as shown below:

Column 1,
Line 6, before "FIELD OF THE INVENTION" include the following:

-- ACKNOWLEDGMENT OF GOVERNMENT SUPPORT
This invention was made with government support under National Institutes of Health grant no. HL53749. The U.S. government has certain rights in this invention. --

Signed and Sealed this

First Day of July, 2003

JAMES E. ROGAN
*Director of the United States Patent and Trademark Office*

UNITED STATES PATENT AND TRADEMARK OFFICE
CERTIFICATE OF CORRECTION

PATENT NO. : 6,344,445 B1
DATED : February 5, 2002
INVENTOR(S) : Boursnell et al.

It is certified that error appears in the above-identified patent and that said Letters Patent is hereby corrected as shown below:

Title page, Item [54] and Column 1, lines 1-2,
Title, "HERPES VIRUS VECTORS AND THEIR USES", should be -- METHOD OF TRANSDUCING HEMOPOIETIC CELLS WITH A NON-TRANSFORMING HERPES VIRUS --

Column 9,
Line 66, error reads "specification.", should be -- specification --

Column 15,
Line 12, error reads "(pfu)1cell)", should be -- (pfu)/cell),- -

Column 16,
Line 1, error reads "gH-deleted HSV1 and qH-deleted", should be -- gH deleted HSV1 and gH-deleted --

Column 17,
Line 20 error reads "5°", should be -- 5' --
Line 47, error reads "Dilasmids", should be -- plasmids --

Column 18,
Line 14, error reads "Kienow", should be -- Klenow --

Column 20,
At the end of the first line of the sequence listing, "SEQ ID NO:16" is in the wrong place, should be at the end of the sequence listing
Line 21, of the sequence listing, error reads "ATGGCCCACG", should be -- ATGGCCCACG --
At the end of the first line of the sequence listing, "SEQ ID NO:17" is in the wrong place, should be at the end of the sequence listing Column 26,
Line 24, error reads "Wash", should be -- WA --
Line 28, error reads "MOI)", should be -- (MOI) --
Line 35, error reads "Colo", should be -- CO --
Line 36, error reads "6", should be -- -6 --
Line 36, error reads "4", should be -- -4 --

UNITED STATES PATENT AND TRADEMARK OFFICE
CERTIFICATE OF CORRECTION

PATENT NO. : 6,344,445 B1
DATED : February 5, 2002
INVENTOR(S) : Boursnell et al.

It is certified that error appears in the above-identified patent and that said Letters Patent is hereby corrected as shown below:

Column 28,
Line 18, error reads "CD34", should be -- CD34+ --

Column 40,
Line 12, error reads "tan", should be -- than --

Signed and Sealed this

Twentieth Day of April, 2004

JON W. DUDAS
*Acting Director of the United States Patent and Trademark Office*

SEQUENCE LISTING (1) GENERAL INFORMATION:

(iii) NUMBER OF SEQUENCES: 25

(2) INFORMATION FOR SEQ ID NO: 1:

(i) SEQUENCE CHARACTERISTICS:
        (A) LENGTH: 17 base pairs
        (B) TYPE: nucleic acid
        (C) STRANDEDNESS: single
        (D) TOPOLOGY: linear (iii) HYPOTHETICAL: NO (iii) ANTI-SENSE: NO (xi) SEQUENCE DESCRIPTION: SEQ ID NO: 1:

AGCTTAGTAC TGACGAC                                            17

(2) INFORMATION FOR SEQ ID NO: 2:

(i) SEQUENCE CHARACTERISTICS:
        (A) LENGTH: 17 base pairs
        (B) TYPE: nucleic acid
        (C) STRANDEDNESS: single
        (D) TOPOLOGY: linear (iii) HYPOTHETICAL: NO (iii) ANTI-SENSE: NO (xi) SEQUENCE DESCRIPTION: SEQ ID NO: 2:

CATGGTCGTC AGTACTA                                            17

(2) INFORMATION FOR SEQ ID NO: 3:

(i) SEQUENCE CHARACTERISTICS:
        (A) LENGTH: 24 base pairs
        (B) TYPE: nucleic acid
        (C) STRANDEDNESS: single
        (D) TOPOLOGY: linear (iii) HYPOTHETICAL: NO (iii) ANTI-SENSE: NO (xi) SEQUENCE DESCRIPTION: SEQ ID NO: 3:

GTGGAGACGC GAATAATCGC GAGC                                       24

(2) INFORMATION FOR SEQ ID NO: 4:

(i) SEQUENCE CHARACTERISTICS:
        (A) LENGTH: 32 base pairs
        (B) TYPE: nucleic acid
        (C) STRANDEDNESS: single
        (D) TOPOLOGY: linear (iii) HYPOTHETICAL: NO (iii) ANTI-SENSE: NO (xi) SEQUENCE DESCRIPTION: SEQ ID NO: 4:

GGCCGCTCGC GATTATTCGC GTCTCCACAA AA                             32

(2) INFORMATION FOR SEQ ID NO: 5:

(i) SEQUENCE CHARACTERISTICS:
        (A) LENGTH: 25 base pairs
        (B) TYPE: nucleic acid
        (C) STRANDEDNESS: single
        (D) TOPOLOGY: linear (iii) HYPOTHETICAL: NO (iii) ANTI-SENSE: NO (xi) SEQUENCE DESCRIPTION: SEQ ID NO: 5:

TCGAAGCTTC AGGGAGTGGC GCAGC                                      25

(2) INFORMATION FOR SEQ ID NO: 6:

(i) SEQUENCE CHARACTERISTICS:
        (A) LENGTH: 30 base pairs
        (B) TYPE: nucleic acid
        (C) STRANDEDNESS: single
        (D) TOPOLOGY: linear (iii) HYPOTHETICAL: NO (iii) ANTI-SENSE: NO (xi) SEQUENCE DESCRIPTION: SEQ ID NO: 6:

TCAGTTAACG GACAGCATGG CCAGGTCAAG                             30

(2) INFORMATION FOR SEQ ID NO: 7:

(i) SEQUENCE CHARACTERISTICS:
        (A) LENGTH: 29 base pairs
        (B) TYPE: nucleic acid
        (C) STRANDEDNESS: single
        (D) TOPOLOGY: linear (iii) HYPOTHETICAL: NO (iii) ANTI-SENSE: NO (xi) SEQUENCE DESCRIPTION: SEQ ID NO: 7:

TCAGTTAACG CCTCTGTTCC TTTCCCTTC                                               29

(2) INFORMATION FOR SEQ ID NO: 8:

(i) SEQUENCE CHARACTERISTICS:
        (A) LENGTH: 30 base pairs
        (B) TYPE: nucleic acid
        (C) STRANDEDNESS: single
        (D) TOPOLOGY: linear (iii) HYPOTHETICAL: NO (iii) ANTI-SENSE: NO (xi) SEQUENCE DESCRIPTION: SEQ ID NO: 8:

TCAGAATTCG AGCAGCTCCT CATGTTCGAC                                              30

(2) INFORMATION FOR SEQ ID NO: 9:

(i) SEQUENCE CHARACTERISTICS:
        (A) LENGTH: 29 base pairs
        (B) TYPE: nucleic acid
        (C) STRANDEDNESS: single
        (D) TOPOLOGY: linear (iii) HYPOTHETICAL: NO (iii) ANTI-SENSE: NO (xi) SEQUENCE DESCRIPTION: SEQ ID NO: 9:

TCAGTTAACG CCTCTGTTCC TTTCCCTTC                                               29

(2) INFORMATION FOR SEQ ID NO: 10:

(i) SEQUENCE CHARACTERISTICS:
        (A) LENGTH: 29 base pairs
        (B) TYPE: nucleic acid
        (C) STRANDEDNESS: single
        (D) TOPOLOGY: linear (iii) HYPOTHETICAL: NO (iii) ANTI-SENSE: NO (xi) SEQUENCE DESCRIPTION: SEQ ID NO: 10:

TCAGAATTCG TTCCGGGAGC AGGCGTGGA                                               29

(2) INFORMATION FOR SEQ ID NO: 11:

(i) SEQUENCE CHARACTERISTICS:
        (A) LENGTH: 30 base pairs
        (B) TYPE: nucleic acid
        (C) STRANDEDNESS: single
        (D) TOPOLOGY: linear (iii) HYPOTHETICAL: NO (iii) ANTI-SENSE: NO (xi) SEQUENCE DESCRIPTION: SEQ ID NO: 11:

TCAAAGCTTA TGGCTTCTCA CGCCGGCCAA                                              30

(2) INFORMATION FOR SEQ ID NO: 12:

(i) SEQUENCE CHARACTERISTICS:

(A) LENGTH: 35 base pairs
    (B) TYPE: nucleic acid
    (C) STRANDEDNESS: single
    (D) TOPOLOGY: linear (iii) HYPOTHETICAL: NO (iii) ANTI-SENSE: NO (xi) SEQUENCE DESCRIPTION: SEQ ID NO: 12:

TCAGTTAACT GCACTAGTTT TAATTAATAC GTATG                                    35

(2) INFORMATION FOR SEQ ID NO: 13:

(i) SEQUENCE CHARACTERISTICS:
        (A) LENGTH: 40 base pairs
        (B) TYPE: nucleic acid
        (C) STRANDEDNESS: single
        (D) TOPOLOGY: linear (iii) HYPOTHETICAL: NO (iii) ANTI-SENSE: NO (xi) SEQUENCE DESCRIPTION: SEQ ID NO: 13:

TGGATGACAT GCCTGTCACA TTGAATGAAG AGGTAGAAGT                               40

(2) INFORMATION FOR SEQ ID NO: 14:

(i) SEQUENCE CHARACTERISTICS:
        (A) LENGTH: 36 base pairs
        (B) TYPE: nucleic acid
        (C) STRANDEDNESS: single
        (D) TOPOLOGY: linear (iii) HYPOTHETICAL: NO (iii) ANTI-SENSE: NO (xi) SEQUENCE DESCRIPTION: SEQ ID NO: 14:

GGCCGCTCGA ACATGGCCCA CGAGAGAAAG GCTAAG                                   36

(2) INFORMATION FOR SEQ ID NO: 15:

(i) SEQUENCE CHARACTERISTICS:
        (A) LENGTH: 35 base pairs
        (B) TYPE: nucleic acid
        (C) STRANDEDNESS: single
        (D) TOPOLOGY: linear (iii) HYPOTHETICAL: NO (iii) ANTI-SENSE: NO (xi) SEQUENCE DESCRIPTION: SEQ ID NO: 15:

GACCTTAGCC TTTCTCTCGT GGGCCATGTT CGAGC                                    35

(2) INFORMATION FOR SEQ ID NO: 16:

(i) SEQUENCE CHARACTERISTICS:
        (A) LENGTH: 170 base pairs
        (B) TYPE: nucleic acid
        (C) STRANDEDNESS: single
        (D) TOPOLOGY: linear (iii) HYPOTHETICAL: NO (iii) ANTI-SENSE: NO (xi) SEQUENCE DESCRIPTION: SEQ ID NO: 16:

```
TTAATACGAC TCACTATAGG GAGACCGGAA GCTTGGTACC GAGCTCGGAT CCACTAGTAA       60

CGGCCGCCAG TGTGCTGGAA TTCTGCAGAT ATCCATCACA CTGGCGGCCG CTCGAGCATG      120

CATCTAGCCT TTTGACTACA ATGGCCCACG AGAGAAAGGC TAAGGTCCTG                 170
```

(2) INFORMATION FOR SEQ ID NO: 17:

(i) SEQUENCE CHARACTERISTICS:
        (A) LENGTH: 147 base pairs
        (B) TYPE: nucleic acid
        (C) STRANDEDNESS: single
        (D) TOPOLOGY: linear (iii) HYPOTHETICAL: NO (iii) ANTI-SENSE: NO (xi) SEQUENCE DESCRIPTION: SEQ ID NO: 17:

```
TTAATACGAC TCACTATAGG GAGACCGGAA GCTTGGTACC GAGCTCGGAT CCACTAGTAA       60

CGGCCGCCAG TGTGCTGGAA TTCTGCAGAT ATCCATCACA CTGGCGGCCG CTCGAACATG      120

GCCCACGAGA GAAAGGCTAA GGTCCTG                                         147
```

(2) INFORMATION FOR SEQ ID NO: 18:

(i) SEQUENCE CHARACTERISTICS:
        (A) LENGTH: 25 base pairs
        (B) TYPE: nucleic acid
        (C) STRANDEDNESS: single
        (D) TOPOLOGY: linear (iii) HYPOTHETICAL: NO (iii) ANTI-SENSE: NO (xi) SEQUENCE DESCRIPTION: SEQ ID NO: 18:

```
TCGAAGCTTC AGGGAGTGGC GCAGC                                            25
```

(2) INFORMATION FOR SEQ ID NO: 19:

(i) SEQUENCE CHARACTERISTICS:
        (A) LENGTH: 30 base pairs
        (B) TYPE: nucleic acid
        (C) STRANDEDNESS: single
        (D) TOPOLOGY: linear (iii) HYPOTHETICAL: NO (iii) ANTI-SENSE: NO (xi) SEQUENCE DESCRIPTION: SEQ ID NO: 19:

```
TCAGTTAACG GCCAGCATAG CCAGGTCAAG                                       30
```

(2) INFORMATION FOR SEQ ID NO: 20:

(i) SEQUENCE CHARACTERISTICS:
        (A) LENGTH: 30 base pairs
        (B) TYPE: nucleic acid
        (C) STRANDEDNESS: single
        (D) TOPOLOGY: linear (iii) HYPOTHETICAL: NO (iii) ANTI-SENSE: NO (xi) SEQUENCE DESCRIPTION: SEQ ID NO: 20:

```
TCAGTTAACA GCCCCTCTTT GCTTTCCCTC                                       30
```

(2) INFORMATION FOR SEQ ID NO: 21:

(i) SEQUENCE CHARACTERISTICS:
        (A) LENGTH: 30 base pairs
        (B) TYPE: nucleic acid
        (C) STRANDEDNESS: single
        (D) TOPOLOGY: linear (iii) HYPOTHETICAL: NO (iii) ANTI-SENSE: NO (xi) SEQUENCE DESCRIPTION: SEQ ID NO: 21:

TCAGAATTCG AGCAGCTCCT CATGTTCGAC          30

(2) INFORMATION FOR SEQ ID NO: 22:

(i) SEQUENCE CHARACTERISTICS:
        (A) LENGTH: 30 base pairs
        (B) TYPE: nucleic acid
        (C) STRANDEDNESS: single
        (D) TOPOLOGY: linear (iii) HYPOTHETICAL: NO (iii) ANTI-SENSE: NO (xi) SEQUENCE DESCRIPTION: SEQ ID NO: 22:

TCAAAGCTTA TGGCTTCGTA CCCCTGCCAT          30

(2) INFORMATION FOR SEQ ID NO: 23:

(i) SEQUENCE CHARACTERISTICS:
        (A) LENGTH: 30 base pairs
        (B) TYPE: nucleic acid
        (C) STRANDEDNESS: single
        (D) TOPOLOGY: linear (iii) HYPOTHETICAL: NO (iii) ANTI-SENSE: NO (xi) SEQUENCE DESCRIPTION: SEQ ID NO: 23:

TCAGTTAACG GACCCCGTCC CTAACCCACG          30

(2) INFORMATION FOR SEQ ID NO: 24:

(i) SEQUENCE CHARACTERISTICS:
        (A) LENGTH: 30 base pairs
        (B) TYPE: nucleic acid
        (C) STRANDEDNESS: single
        (D) TOPOLOGY: linear (iii) HYPOTHETICAL: NO (iii) ANTI-SENSE: NO (xi) SEQUENCE DESCRIPTION: SEQ ID NO: 24:

TCAGTTAACA GCCCCTCTTT GCTTTCCCTC          30

(2) INFORMATION FOR SEQ ID NO: 25:

(i) SEQUENCE CHARACTERISTICS:
        (A) LENGTH: 30 base pairs
        (B) TYPE: nucleic acid
        (C) STRANDEDNESS: single
        (D) TOPOLOGY: linear (iii) HYPOTHETICAL: NO (iii) ANTI-SENSE: NO (xi) SEQUENCE DESCRIPTION: SEQ ID NO: 25:

TCAGAATTCG AGCAGCTCCT CATGTTCGAC                              30